United States Patent
Dibas et al.

(10) Patent No.: US 11,077,053 B2
(45) Date of Patent: Aug. 3, 2021

(54) ALPHA-2-ADRENERGIC RECEPTOR AGONISTS FOR TREATMENT OF PRESBYOPIA, VISUAL GLARE, VISUAL STARBURSTS, VISUAL HALOS AND NIGHT MYOPIA

(71) Applicant: Allergan, Inc., Irvine, CA (US)

(72) Inventors: Mohammed Dibas, Corona, CA (US); Daniel W. Gil, Corona Del Mar, CA (US); Wayne Chen, Costa Mesa, CA (US); Miguel Alcantara, Aliso Viejo, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 16/950,574

(22) Filed: Nov. 17, 2020

(65) Prior Publication Data
US 2021/0059930 A1    Mar. 4, 2021

Related U.S. Application Data

(63) Continuation of application No. 17/055,922, filed as application No. PCT/US2019/047305 on Aug. 20, 2019.
(Continued)

(51) Int. Cl.
*A61K 9/00* (2006.01)
*A61P 27/02* (2006.01)
(Continued)

(52) U.S. Cl.
CPC ........ *A61K 9/0048* (2013.01); *A61K 31/4178* (2013.01); *A61P 27/02* (2018.01); *A61P 27/10* (2018.01)

(58) Field of Classification Search
CPC ... A61K 9/0048; A61K 31/4178; A61P 27/02; A61P 27/10
See application file for complete search history.

(56) References Cited

U.S. PATENT DOCUMENTS

| 5,424,078 A | 6/1995 | Dziabo et al. |
| 5,478,858 A * | 12/1995 | Cupps ............ A61P 27/16 514/394 |

(Continued)

FOREIGN PATENT DOCUMENTS

| WO | 9325199 | 12/1993 |
| WO | 9516685 | 6/1995 |

(Continued)

OTHER PUBLICATIONS

Berge, Stephen M., Pharmaceutical Salts, Journal of Pharmaceutical Sciences, Jan. 1977, 1-19, 66 (1), US.
(Continued)

*Primary Examiner* — Carlos A Azpuru
(74) *Attorney, Agent, or Firm* — Jonathan Bass

(57) ABSTRACT

Methods of using the alpha-2-adrenergic receptor agonist of Formula I:

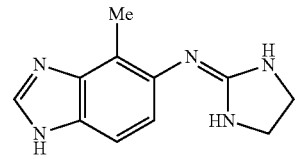

Formula I for improving vision such as in the treatment of ocular conditions such as presbyopia, poor night vision, visual
(Continued)

glare, visual starbursts, visual halos, and some forms of myopia (e.g. night myopia) are described.

11 Claims, 7 Drawing Sheets

Related U.S. Application Data

(60) Provisional application No. 62/720,671, filed on Aug. 21, 2018.

(51) Int. Cl.
*A61P 27/10* (2006.01)
*A61K 31/4178* (2006.01)

(56) References Cited

U.S. PATENT DOCUMENTS

| | | | |
|---|---|---|---|
| 6,495,583 B1 * | 12/2002 | Jeon | C07D 403/12 514/394 |
| 7,037,943 B2 | 5/2006 | Peyman et al. | |
| 8,829,037 B2 | 9/2014 | Sharma | |
| 9,289,413 B2 | 3/2016 | Hughes et al. | |
| 9,504,653 B2 | 11/2016 | Liu et al. | |
| 9,597,328 B2 | 3/2017 | Jain et al. | |
| 9,844,537 B2 | 12/2017 | Horn et al. | |
| 9,867,810 B1 | 1/2018 | Feinbaum et al. | |
| 10,117,868 B2 | 11/2018 | Palczewski et al. | |
| 10,555,947 B2 | 2/2020 | Musunuri et al. | |
| 2002/0082288 A1 | 6/2002 | Horn | |
| 2008/0260832 A1 | 10/2008 | Burke et al. | |
| 2011/0182966 A1 | 7/2011 | Robinson et al. | |
| 2012/0328687 A1 | 12/2012 | Horn | |
| 2016/0022695 A1 | 1/2016 | Reich et al. | |
| 2016/0296532 A1 | 10/2016 | Stark et al. | |
| 2016/0331745 A1 | 11/2016 | Shah et al. | |
| 2019/0224120 A1 | 7/2019 | Horn | |

FOREIGN PATENT DOCUMENTS

| | | |
|---|---|---|
| WO | 9604270 | 2/1996 |
| WO | 9823595 | 6/1998 |
| WO | 2011091225 | 7/2011 |
| WO | 2014015183 | 1/2014 |
| WO | 2017160548 | 9/2017 |
| WO | 2019230834 | 12/2019 |

OTHER PUBLICATIONS

Charman, W., The eye in focus: accommodation and presbyopia, Clin. Exp. Optometry, 2008, 207-225, 91(3).
Chee, Soon-Phaik, Moxifloxacin Punctum Plug for Sustained Drug Delivery, Journal of Ocular Pharmacology and Therapeutics, 2012, 340-349, 28 (4).
Edwards, J., et al., Effect of brimonidine tartrate 0.15% on night-vision difficulty and contrast testing after refractive surgery, Journal of Cataract & Refractive Surgery, 2008, 1538-1541, 34 (9).
Farr, J., The KAMRA® Corneal Inlay Brings Life Back into Focus for Patients with Presbyopia, Blurring Near Vision, https://kamra.com/news/the-kamra-corneal-inlay-brings-life-back-into-focus-for-patients- . . . , 2018, pp. 1-5.
Food & Drug Administration, Isopto Carpine Prescribing Information, FDA Access Data, 2006, 5 pages.
Franssen, L., et al., Grading of Iris Color with an Extended Photographic Reference Set, J. Optom., 2008, 36-40, 1(1).
Freeman, D, et al., Preservatives in Topical Ophthalmic Medications: Historical and Clinical Perspectives, Expert Rev. Ophthalmol., 2009, 59-64, 4 (1).
Haddrill, M., Glaucoma Treatment: Eye Drops and Other Medications, http://www.allaboutvision.com/conditions/glaucoma-3-treatment.htm, 2018, pp. 1-5.
Heinrich Stahl, Handbook of Pharmaceutical Salts, Properties, Selection, and Use, Handbook of Pharmaceutical Salts, Properties, Selection, and Use, 2002, 329-345, N/A.
Kuno, N., et al., Recent Advances in Ocular Drug Delivery Systems, Polymers, 2011, 193-221, 3.
Lee, J., et al., Efficacy of brimonidine tartrate 0.2% ophthalmic solution in reducing halos after laser in situ keratomileusis, J. Cataract Refract. Surg., 2008, 963-967, 34.
Mac Donald, J. et al., Effect of brimonidine tartrate ophthalmic solution 0.2% on pupil size in normal eyes under different luminance conditions, J Cataract Refract Surg, 2001, 560-564, 27.
Plainis, S., et al., Reduced-aperture monovision for presbyopia and the Pulfrich effect, Journal of Optometry, 2012, 156-163, 5.
Tejpal, Y. et al., Microspheres as an Ocular Drug Delivery System-A Review, Journal of Drug Delivery & Therapeutics, 2013, 114-123, 3 (1).
Unknown, 1.5 years post op Lasik, my night vision Is still bad and I see star bursting/halos. Will I still see improvements?, RealSelf.com, 2018, pp. 1-3.
Unknown, Halos after LASIK, http://www.lasikcomplications.com/halos.htm, 2018, pp. 1-3.
Unknown, Post-LASIK patients risk of halos and starbursts around bright ligths at night, https://www.londonvisionclinic.com/post-lasik-patients-risk-of-halos-and-starbursts-around-bright-lights-at-night/, 2018, pp. 1-11.
Unknown, Safety, Tolerability, and Efficacy of PresblDrops (CSF-1), a Topical Ophthalmic Drug for Presbyopia, ClinicalTrails.gov, 2018, pp. 1-9.
Unknown, Starburts after LASIK, http://www.lasikcomplications.com/starbursting.htm, 2018, pp. 1-3.
Unknown, The Safety and Efficacy of Phentolamine Mesylate Ophthalmic Solution in Subjects With Severe Night Vision Complaints, ClinicalTrails.gov, 2018, pp. 1-8.
Xu, R., et al., The effect of light level and small pupils on presbyoplc reading performance, IVOS, 2016, 5656-5664, 57 (13).
PCT International Search Report and Written Opinion dated Nov. 19, 2019, for PCT/US2019/047305, flied Aug. 20, 2019, in the name of Allergan, Inc.
Garcia-Lozara, S., et al., Visual function through 4 contact lens-based pinhole systems for presbyopia, J. Cataract Refract. Surg., 2012, 858-865, 38 (5).
Holden, B.A, et al., Global vision impairment due to uncorrected presbyopia, Arch. Ophthalmology, 2008, 1731-1739, 126.
Hunkeler, J., et al., Characterization of visual phenomena with the Array multifocal intraocular lens, J Cataract Refract. Surg., 2002, 1195-1204, 28.
Johnson, L., et al, Multifocal spectacles increase variability in toe clearance and risk of tripping in the elderly, IVOS, 2007, 1466-1471, 48.
Lord, S.R., et al, Multifocal glasses impair edge-contrast sensitivity and depth perception and increase the risk of falls in older people, J. Am. Geriatric Society, 2002, 1760-1768, 50.
Moishirfar, M., et al, Comparison of FDA safety and efficacy data for KAMRA and Raindrop corneal inlays, int. J. Ophthalmol., 2017, 1446-1451, 10 (9).
Pilocarpine hydrochloride ophthalmic solution 1%, 2%, and 4%. Package Insert. Fort Worth, TX: Alcon Laboratories, Inc. 2011.
Ruiz, L.A., et al, Intrastromal correction of presbyopia using femtosecond laser system, J. Refract. Surg., 2009, 847-854, 25 (10).
Rundfeldt, C., Multi-Dose Container for Nasal and Ophthalmic Drugs: A Preservative Free Future?, Drug Development-A Case Study Based Insight into Modern Strategies, 2011, 509-522, Ch. 20.
Tomita, M., Advances in Implantation over the Years, Cataract & Refractive Surgery Today, 2015, 67-68.
Tucker, J. et al, The depth-of-focus of the human eye for Snellen letters, Am. J. Optom. Physiol. Opt., 1975, 3-21, 52 (1).
Xu, R., et al., Reducing starbursts in highly aberrated eyes with pupil miosis, Ophthalmic Physiol. Opt., 2018, 26-36, 38.
Novack, G., Emerging drugs for ophthalmic diseases, Expert Opinion on Emerging Drugs, 2003, 251-266, 8 (1).

* cited by examiner

ALPHA-2-ADRENERGIC RECEPTOR AGONISTS FOR TREATMENT OF PRESBYOPIA, VISUAL GLARE, VISUAL STARBURSTS, VISUAL HALOS AND NIGHT MYOPIA

CROSS-REFERENCE TO RELATED APPLICATIONS

This application is a continuation of U.S. patent application Ser. No. 17/055,922, filed Nov. 16, 2020, which is a US national phase application under 35 USC 371 of PCT application PCT/US2019/047305, filed Aug. 20, 2019, which claims the benefit of and/or priority to U.S. provisional application 62/720,671 filed on Aug. 21, 2018, all of which are incorporated by reference herein in their entireties and which serve as the basis of a priority and/or benefit claim for the present application.

FIELD

The present invention relates generally to uses of compounds for improving vision in individuals. The invention relates in particular to the use of alpha-2-adrenergic receptor agonists for improving vision such as in the treatment of ocular conditions such as presbyopia, poor night vision, visual glare, visual starbursts, visual halos, and some forms of myopia (e.g. night myopia).

BACKGROUND

Presbyopia is the gradual loss of eyes' ability to focus on near objects, which can interfere with everyday tasks such as reading, operating a smartphone or tablet, or working on a computer. With age, the lens loses its flexibility which results in gradual loss of accommodation and therefore losing its ability to focus on near objects. This reduced lens flexibility results in image blur and loss of acuity, which is exacerbated by pupil dilation (such as occurs in low light conditions). Presbyopia starts to appear in a person's early- to mid-forties and worsens up to about age 65. To correct reading vision, patients suffering from presbyopia often seek several treatment options such as reading glasses, contact lenses, and intraocular lenses, as well as surgical alternatives such as refractive lens exchange. Although reading glasses can be simple and inexpensive, there could be associated inconveniences and aesthetic concerns, and wearing bifocal glasses has been associated with increased risk of fall in senior citizens. One alternative to the inconveniences and problems associated with glasses, as well as to invasive surgical options for treatment of presbyopia, is to constrict pupil size with miotic agents.

Additionally, one side-effect of LASIK surgery is aberrations of peripheral corneal curvature which can permit additional light to enter the eye resulting in visual disturbances such as visual glare, visual starbursts, and visual halos, especially in low light conditions when the pupil is dilated. By constricting the pupil, this aberrant peripheral light can be blocked and the visual disturbances reduced. Indeed, brimonidine (ALPHAGAN® P), an ophthalmic alpha-2-adrenergic receptor agonist that decreases pupil size in patients, is used to reduce glare and starburst in patients post LASIK surgery. In a similar manner, some people experience myopia only at night due to pupil dilation which can allow additional peripheral unfocused light rays to enter the eye resulting in blurred distance vision. Such individuals could also benefit from a reduction in pupil size.

However, in spite of the fact brimonidine is occasionally used to reduce pupil size, it often loses its efficacy after chronic use, is less effective in individuals with dark irises and it is short acting. Therefore, there is a need for improved and longer-acting methods of reducing pupil size, such as those described herein, to treat ocular conditions such as presbyopia, poor night vision, visual glare, visual starbursts, and visual halos, and some forms of myopia (e.g. night myopia).

SUMMARY

Disclosed herein are methods of improving vision in subjects in need thereof, as well as methods of treating ocular conditions in individuals in need thereof.

In a first aspect, described herein is a method of treating of one or more ocular conditions (for example, presbyopia, poor night vision, visual glare, visual starbursts, visual halos, and some forms of myopia (e.g. night myopia)) by administering to the individual a therapeutically effective amount of a compound of Formula I:

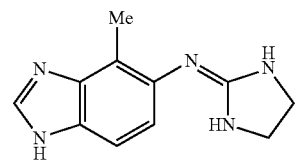

Formula I or a pharmaceutically acceptable salt thereof.

In another aspect, described herein are methods of treating ocular conditions in and individual in need thereof by administering to the individual a therapeutically effective amount of a compound of Formula I or a pharmaceutically acceptable salt thereof.

Some non-limiting example embodiments are given below.

Example embodiment 1: A method of treating an ocular condition in an individual in need of such treatment, the method comprising administering to the individual a therapeutically effective amount of a compound of Formula I:

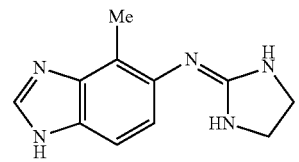

Formula I or a pharmaceutically acceptable salt thereof, and wherein the ocular condition is selected from the group consisting of presbyopia, poor night vision, visual glare, visual starbursts, visual halos, and night myopia.

Example embodiment 2: The method of example embodiment 1, wherein the ocular condition is presbyopia.

Example embodiment 3: The method of example embodiment 1, wherein the ocular condition is poor night vision.

Example embodiment 4: The method of example embodiment 1, wherein the ocular condition is visual glare.

Example embodiment 5: The method of example embodiment 1, wherein the ocular condition is visual starbursts.

Example embodiment 6: The method of example embodiment 1, wherein the ocular condition is visual halos.

Example embodiment 7: The method of example embodiment 1, wherein the ocular condition is night myopia.

Example embodiment 8: The method of any one of example embodiments 1-7, wherein the compound of Formula I or a pharmaceutically acceptable salt thereof is administered to one or both eyes of the individual.

Example embodiment 9: The method of example embodiment 8, wherein the administration to the eye is topical administration.

Example embodiment 10: The method of any one of example embodiments 1-9, wherein the therapeutically effective amount of the compound of Formula I or pharmaceutically acceptable salt thereof is administered to the individual as a pharmaceutically acceptable composition comprising the therapeutically effective amount of the compound of Formula I or a pharmaceutically acceptable salt thereof and a pharmaceutically acceptable excipient.

Example embodiment 11: The method of example embodiment 10, wherein the pharmaceutically acceptable composition comprises the compound of Formula I in an amount of 0.01% (w/v).

Example embodiment 12: The method of example embodiment 10, wherein the pharmaceutically acceptable composition comprises the compound of Formula I in an amount of 0.03% (w/v).

Example embodiment 13: The method of example embodiment 10, wherein the pharmaceutically acceptable composition comprises the compound of Formula I in an amount of 0.1% (w/v).

Example embodiment 14: The method of example embodiment 10, wherein the pharmaceutically acceptable composition comprises the compound of Formula I in an amount of 0.3% (w/v).

Example embodiment 15: The method of example embodiment 10, wherein the pharmaceutically acceptable composition is an ocular implant, intracameral implant, intravitreal implant, subconjunctival implant, sub-Tenon's implant, punctum plug, canicular eluting implant, or ocular ring.

Example embodiment 16: The method of example embodiment 10, wherein the pharmaceutically acceptable composition is a microsphere.

Example embodiment 17: The method of any one of example embodiment 1-16, wherein the therapeutically effective amount of the compound of Formula I or pharmaceutically acceptable salt thereof, when administered to the individual, has binding to the iris pigment that is less than the binding to the iris pigment exhibited by brimonidine.

Example embodiment 18: The method of any one of example embodiments 1-16, wherein the therapeutically effective amount of the compound of Formula I or pharmaceutically acceptable salt thereof is an amount that is less than the amount of brimonidine needed to achieve the same therapeutic effects.

Example embodiment 19: The method of any one of example embodiments 1-16, wherein the therapeutically effective amount of the compound of Formula I or pharmaceutically acceptable salt thereof, when administered to the individual, causes an amount of reduction in pupil size such that the pupil is constricted to a size of between 2 and 3 mm.

Example embodiment 20: The method of any one of example embodiments 1-16, wherein the therapeutically effective amount of the compound of Formula I or pharmaceutically acceptable salt thereof, when administered to the individual, causes an amount of reduction in pupil size such that the pupil is constricted to a size of 3 mm or less.

Example embodiment 21: The method of any one of example embodiments 1-16, wherein the therapeutically effective amount of the compound of Formula I or pharmaceutically acceptable salt thereof, when administered to the individual, causes an amount of reduction in pupil size such that the pupil is constricted to a size of 2.5 mm or less.

Example embodiment 22: The method of any one of example embodiments 1-16, wherein the therapeutically effective amount of the compound of Formula I or pharmaceutically acceptable salt thereof, when administered to the individual, causes an improvement in near visual acuity.

Example embodiment 23: The method of any one of example embodiments 1-16, wherein the therapeutically effective amount of the compound of Formula I or pharmaceutically acceptable salt thereof, when administered to the individual, causes an improvement in intermediate visual acuity.

Example embodiment 24: The method of any one of example embodiments 1-16, wherein the therapeutically effective amount of the compound of Formula I or pharmaceutically acceptable salt thereof, when administered to the individual, causes an improvement in distance visual acuity.

Example embodiment 25: The method of any one of example embodiments 22-24, where in the improvement in visual acuity is an at least 2-line improvement.

Example embodiment 26: The method of any one of example embodiments 22-24, where in the improvement in visual acuity is an at least 3-line improvement.

Example embodiment 27: The method of any one of example embodiments 19-26, wherein the reduction in pupil size or improvement in visual acuity is maintained for at least 1 hour.

Example embodiment 28: The method of any one of example embodiments 19-26, wherein the reduction in pupil size or improvement in visual acuity is maintained for at least 2 hours.

Example embodiment 29: The method of any one of example embodiments 19-26, wherein the reduction in pupil size or improvement in visual acuity is maintained for at least 4 hours.

Example embodiment 30: The method of any one of example embodiments 19-26, wherein the reduction in pupil size or improvement in visual acuity is maintained for at least 6 hours.

Example embodiment 31: The method of any one of example embodiments 19-26, wherein the reduction in pupil size or improvement in visual acuity is maintained for at least 9 hours.

Example embodiment 32: The method of any one of example embodiments 19-26, wherein the reduction in pupil size or improvement in visual acuity is maintained for at least 10 hours.

Example embodiment 33: The method of any one of example embodiments 19-26, wherein the reduction in pupil size or improvement in visual acuity is maintained for at least 12 hours.

Example embodiment 34: The method of any one of example embodiments 19-33, wherein the reduction in pupil size or improvement in visual acuity is achieved when the individual is exposed to luminance levels of less than 200 cd/m$^2$.

Example embodiment 35: The method of any one of example embodiments 19-33, wherein the reduction in pupil size or improvement in visual acuity is achieved when the individual is exposed to luminance levels of less than 150 cd/m$^2$.

Example embodiment 36: The method of any one of example embodiments 19-33, wherein the reduction in pupil size or improvement in visual acuity is achieved when the individual is exposed to luminance levels of less than 100 cd/m$^2$.

Example embodiment 37: The method of any one of example embodiments 19-33, wherein the reduction in pupil size or improvement in visual acuity is achieved when the individual is exposed to luminance levels of less than 50 cd/m$^2$.

Example embodiment 38: The method of any one of example embodiments 19-33, wherein the reduction in pupil size or improvement in visual acuity is achieved when the individual is exposed to luminance levels of less than 10 cd/m$^2$.

Example embodiment 39: The method of any one of example embodiments 19-33, wherein the reduction in pupil size or improvement in visual acuity is achieved when the individual is exposed to luminance levels of less than 5 cd/m$^2$.

Example embodiment 40: The method of any one of example embodiments 19-33, wherein the reduction in pupil size or improvement in visual acuity is achieved when the individual is exposed to luminance levels of less than 2 cd/m$^2$.

Example embodiment 41: A compound of Formula I:

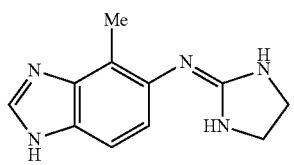

Formula I or a pharmaceutically acceptable salt thereof, for use in a method of treating an ocular condition in an individual in need thereof, the method comprising administering to the individual a therapeutically effective amount of the compound of Formula I or a pharmaceutically acceptable salt thereof, and wherein the ocular condition is selected from the group consisting of presbyopia, poor night vision, visual glare, visual starbursts, visual halos, and night myopia.

Example embodiment 42: The compound or pharmaceutically acceptable salt thereof for use according to example embodiment 41, wherein the ocular condition is presbyopia.

Example embodiment 43: The compound or pharmaceutically acceptable salt thereof for use according to example embodiment 41, wherein the ocular condition is poor night vision.

Example embodiment 44: The compound or pharmaceutically acceptable salt thereof for use according to example embodiment 41, wherein the ocular condition is visual glare.

Example embodiment 45: The compound or pharmaceutically acceptable salt thereof for use according to example embodiment 41, wherein the ocular condition is visual starbursts.

Example embodiment 46: The compound or pharmaceutically acceptable salt thereof for use according to example embodiment 41, wherein the ocular condition is visual halos.

Example embodiment 47: The compound or pharmaceutically acceptable salt thereof for use according to example embodiment 41, wherein the ocular condition is night myopia.

Example embodiment 48: The compound or pharmaceutically acceptable salt thereof for use according to any one of example embodiments 41-47, wherein the compound of Formula I or a pharmaceutically acceptable salt thereof is administered to one or both eyes of the individual.

Example embodiment 49: The compound or pharmaceutically acceptable salt thereof for use according to example embodiment 48, wherein the administration to the eye is topical administration.

Example embodiment 50: The compound or pharmaceutically acceptable salt thereof for use according to any one of example embodiments 41-49, wherein the therapeutically effective amount of the compound of Formula I or pharmaceutically acceptable salt thereof is administered to the individual as a pharmaceutically acceptable composition comprising the therapeutically effective amount of the compound of Formula I or a pharmaceutically acceptable salt thereof and a pharmaceutically acceptable excipient.

Example embodiment 51: The compound or pharmaceutically acceptable salt thereof for use according to example embodiment 50, wherein the pharmaceutically acceptable composition comprises the compound of Formula I in an amount of 0.01% (w/v).

Example embodiment 52: The compound or pharmaceutically acceptable salt thereof for use according to example embodiment 50, wherein the pharmaceutically acceptable composition comprises the compound of Formula I in an amount of 0.03% (w/v).

Example embodiment 53: The compound or pharmaceutically acceptable salt thereof for use according to example embodiment 50, wherein the pharmaceutically acceptable composition comprises the compound of Formula I in an amount of 0.1% (w/v).

Example embodiment 54: The compound or pharmaceutically acceptable salt thereof for use according to example embodiment 50, wherein the pharmaceutically acceptable composition comprises the compound of Formula I in an amount of 0.3% (w/v).

Example embodiment 55: The compound or pharmaceutically acceptable salt thereof for use according to example embodiment 50, wherein the pharmaceutically acceptable composition is an ocular implant, intracameral implant, intravitreal implant, subconjunctival implant, sub-Tenon's implant, punctum plug, canicular eluting implant, or ocular ring.

Example embodiment 56: The compound or pharmaceutically acceptable salt thereof for use according to example embodiment 50, wherein the pharmaceutically acceptable composition is a microsphere.

Example embodiment 57: The compound or pharmaceutically acceptable salt thereof for use according to any one of example embodiments 41-56, wherein the therapeutically effective amount of the compound of Formula I or pharmaceutically acceptable salt thereof, when administered to the individual, has binding to the iris pigment that is less than the binding to the iris pigment exhibited by brimonidine.

Example embodiment 58: The compound or pharmaceutically acceptable salt thereof for use according to any one of example embodiments 41-56, wherein the therapeutically effective amount of the compound of Formula I or pharmaceutically acceptable salt thereof is an amount that is less than the amount of brimonidine needed to achieve the same therapeutic effects.

Example embodiment 59: The compound or pharmaceutically acceptable salt thereof for use according to any one of example embodiments 41-56, wherein the therapeutically effective amount of the compound of Formula I or pharmaceutically acceptable salt thereof, when administered to the individual, causes an amount of reduction in pupil size such that the pupil is constricted to a size of between 2 and 3 mm.

Example embodiment 60: The compound or pharmaceutically acceptable salt thereof for use according to any one of example embodiments 41-56, wherein the therapeutically effective amount of the compound of Formula I or pharmaceutically acceptable salt thereof, when administered to the individual, causes an amount of reduction in pupil size such that the pupil is constricted to a size of 3 mm or less.

Example embodiment 61: The compound or pharmaceutically acceptable salt thereof for use according to any one of example embodiments 41-56, wherein the therapeutically effective amount of the compound of Formula I or pharmaceutically acceptable salt thereof, when administered to the individual, causes an amount of reduction in pupil size such that the pupil is constricted to a size of 2.5 mm or less.

Example embodiment 62: The compound or pharmaceutically acceptable salt thereof for use according to any one of example embodiment 41-56, wherein the therapeutically effective amount of the compound of Formula I or pharmaceutically acceptable salt thereof, when administered to the individual, causes an improvement in near visual acuity.

Example embodiment 63: The compound or pharmaceutically acceptable salt thereof for use according to any one of example embodiments 41-56, wherein the therapeutically effective amount of the compound of Formula I or pharmaceutically acceptable salt thereof, when administered to the individual, causes an improvement in intermediate visual acuity.

Example embodiment 64: The compound or pharmaceutically acceptable salt thereof for use according to any one of example embodiments 41-56, wherein the therapeutically effective amount of the compound of Formula I or pharmaceutically acceptable salt thereof, when administered to the individual, causes an improvement in distance visual acuity.

Example embodiment 65: The compound or pharmaceutically acceptable salt thereof for use according to any one of example embodiments 62-64, where in the improvement in visual acuity is an at least 2-line improvement.

Example embodiment 66: The compound or pharmaceutically acceptable salt thereof for use according to any one of example embodiments 62-64, where in the improvement in visual acuity is an at least 3-line improvement.

Example embodiment 67: The compound or pharmaceutically acceptable salt thereof for use according to any one of example embodiments 59-66, wherein the reduction in pupil size or improvement in visual acuity is maintained for at least 1 hour.

Example embodiment 68: The compound or pharmaceutically acceptable salt thereof for use according to any one of example embodiments 59-66, wherein the reduction in pupil size or improvement in visual acuity is maintained for at least 2 hours.

Example embodiment 69: The compound or pharmaceutically acceptable salt thereof for use according to any one of example embodiments 59-66, wherein the reduction in pupil size or improvement in visual acuity is maintained for at least 4 hours.

Example embodiment 70: The compound or pharmaceutically acceptable salt thereof for use according to any one of example embodiments 59-66, wherein the reduction in pupil size or improvement in visual acuity is maintained for at least 6 hours.

Example embodiment 71: The compound or pharmaceutically acceptable salt thereof for use according to any one of example embodiments 59-66, wherein the reduction in pupil size or improvement in visual acuity is maintained for at least 9 hours.

Example embodiment 72: The compound or pharmaceutically acceptable salt thereof for use according to any one of example embodiments 59-66, wherein the reduction in pupil size or improvement in visual acuity is maintained for at least 10 hours.

Example embodiment 73: The compound or pharmaceutically acceptable salt thereof for use according to any one of example embodiments 59-66, wherein the reduction in pupil size or improvement in visual acuity is maintained for at least 12 hours.

Example embodiment 74: The compound or pharmaceutically acceptable salt thereof for use according to any one of example embodiments 59-73, wherein the reduction in pupil size or improvement in visual acuity is achieved when the individual is exposed to luminance levels of less than 200 cd/m$^2$.

Example embodiment 75: The compound or pharmaceutically acceptable salt thereof for use according to any one of example embodiments 59-73, wherein the reduction in pupil size or improvement in visual acuity is achieved when the individual is exposed to luminance levels of less than 150 cd/m$^2$.

Example embodiment 76: The compound or pharmaceutically acceptable salt thereof for use according to any one of example embodiments 59-73, wherein the reduction in pupil size or improvement in visual acuity is achieved when the individual is exposed to luminance levels of less than 100 cd/m$^2$.

Example embodiment 77: The compound or pharmaceutically acceptable salt thereof for use according to any one of example embodiments 59-73, wherein the reduction in pupil size or improvement in visual acuity is achieved when the individual is exposed to luminance levels of less than 50 cd/m$^2$.

Example embodiment 78: The compound or pharmaceutically acceptable salt thereof for use according to any one of example embodiments 59-73, wherein the reduction in pupil size or improvement in visual acuity is achieved when the individual is exposed to luminance levels of less than 10 cd/m$^2$.

Example embodiment 79: The compound or pharmaceutically acceptable salt thereof for use according to any one of example embodiments 59-73, wherein the reduction in pupil size or improvement in visual acuity is achieved when the individual is exposed to luminance levels of less than 5 cd/m$^2$.

Example embodiment 80: The compound or pharmaceutically acceptable salt thereof for use according to any one of example embodiments 59-73, wherein the reduction in pupil size or improvement in visual acuity is achieved when the individual is exposed to luminance levels of less than 2 cd/m$^2$.

Example embodiment 81: Use of a compound of Formula I:

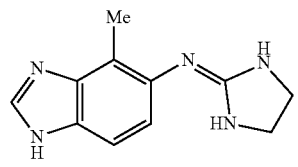

Formula I or a pharmaceutically acceptable salt thereof, in a method of treating an ocular condition in an individual in need thereof, the method comprising administering to the individual a therapeutically effective amount of the compound of Formula I or a pharmaceutically acceptable salt thereof, and wherein the ocular condition is selected from the group consisting of presbyopia, poor night vision, visual glare, visual starbursts, visual halos, and night myopia.

Example embodiment 82: The use according to example embodiment 81, wherein the ocular condition is presbyopia.

Example embodiment 83: The use according to example embodiment 81, wherein the ocular condition is poor night vision.

Example embodiment 84: The use according to example embodiment 81, wherein the ocular condition is visual glare.

Example embodiment 85: The use according to example embodiment 81, wherein the ocular condition is visual starbursts.

Example embodiment 86: The use according to example embodiment 81, wherein the ocular condition is visual halos.

Example embodiment 87: The use according to example embodiment 81, wherein the ocular condition is night myopia.

Example embodiment 88: The use according to any one of example embodiments 81-87, wherein the compound of Formula I or a pharmaceutically acceptable salt thereof is administered to one or both eyes of the individual.

Example embodiment 89: The use according to example embodiment 88, wherein the administration to the eye is topical administration.

Example embodiment 90: The use according to any one of example embodiments 81-89, wherein the therapeutically effective amount of the compound of Formula I or pharmaceutically acceptable salt thereof is administered to the individual as a pharmaceutically acceptable composition comprising the therapeutically effective amount of the compound of Formula I or a pharmaceutically acceptable salt thereof and a pharmaceutically acceptable excipient.

Example embodiment 91: The use according to example embodiment 90, wherein the pharmaceutically acceptable composition comprises the compound of Formula I in an amount of 0.01% (w/v).

Example embodiment 92: The use according to example embodiment 90, wherein the pharmaceutically acceptable composition comprises the compound of Formula I in an amount of 0.03% (w/v).

Example embodiment 93: The use according to example embodiment 90, wherein the pharmaceutically acceptable composition comprises the compound of Formula I in an amount of 0.1% (w/v).

Example embodiment 94: The use according to example embodiment 90, wherein the pharmaceutically acceptable composition comprises the compound of Formula I in an amount of 0.3% (w/v).

Example embodiment 95: The use according to example embodiment 90, wherein the pharmaceutically acceptable composition is an ocular implant, intracameral implant, intravitreal implant, subconjunctival implant, sub-Tenon's implant, punctum plug, canicular eluting implant, or ocular ring.

Example embodiment 96: The use according to example embodiment 90, wherein the pharmaceutically acceptable composition is a microsphere.

Example embodiment 97: The use according to any one of example embodiments 81-96, wherein the therapeutically effective amount of the compound of Formula I or pharmaceutically acceptable salt thereof, when administered to the individual, has binding to the iris pigment that is less than the binding to the iris pigment exhibited by brimonidine.

Example embodiment 98: The use according to any one of example embodiments 81-96, wherein the therapeutically effective amount of the compound of Formula I or pharmaceutically acceptable salt thereof is an amount that is less than the amount of brimonidine needed to achieve the same therapeutic effects.

Example embodiment 99: The use according to any one of example embodiments 81-96, wherein the therapeutically effective amount of the compound of Formula I or pharmaceutically acceptable salt thereof, when administered to the individual, causes an amount of reduction in pupil size such that the pupil is constricted to a size of between 2 and 3 mm.

Example embodiment 100: The use according to any one of example embodiments 81-96, wherein the therapeutically effective amount of the compound of Formula I or pharmaceutically acceptable salt thereof, when administered to the individual, causes an amount of reduction in pupil size such that the pupil is constricted to a size of 3 mm or less.

Example embodiment 101: The use according to any one of example embodiments 81-96, wherein the therapeutically effective amount of the compound of Formula I or pharmaceutically acceptable salt thereof, when administered to the individual, causes an amount of reduction in pupil size such that the pupil is constricted to a size of 2.5 mm or less.

Example embodiment 102: The use according to any one of example embodiments 81-96, wherein the therapeutically effective amount of the compound of Formula I or pharmaceutically acceptable salt thereof, when administered to the individual, causes an improvement in near visual acuity.

Example embodiment 103: The use according to any one of example embodiments 81-96, wherein the therapeutically effective amount of the compound of Formula I or pharmaceutically acceptable salt thereof, when administered to the individual, causes an improvement in intermediate visual acuity.

Example embodiment 104: The use according to any one of example embodiments 81-96, wherein the therapeutically effective amount of the compound of Formula I or pharmaceutically acceptable salt thereof, when administered to the individual, causes an improvement in distance visual acuity.

Example embodiment 105: The use according to any one of example embodiments 102-104, where in the improvement in visual acuity is an at least 2-line improvement.

Example embodiment 106: The use according to any one of example embodiments 102-104, where in the improvement in visual acuity is an at least 3-line improvement.

Example embodiment 107: The use according to any one of example embodiments 99-106, wherein the reduction in pupil size or improvement in visual acuity is maintained for at least 1 hour.

Example embodiment 108: The use according to any one of example embodiments 99-106, wherein the reduction in pupil size or improvement in visual acuity is maintained for at least 2 hours.

Example embodiment 109: The use according to any one of example embodiments 99-106, wherein the reduction in pupil size or improvement in visual acuity is maintained for at least 4 hours.

Example embodiment 110: The use according to any one of example embodiments 99-106, wherein the reduction in pupil size or improvement in visual acuity is maintained for at least 6 hours.

Example embodiment 111: The use according to any one of example embodiments 99-106, wherein the reduction in pupil size or improvement in visual acuity is maintained for at least 9 hours.

Example embodiment 112: The use according to any one of example embodiments 99-106, wherein the reduction in pupil size or improvement in visual acuity is maintained for at least 10 hours.

Example embodiment 113: The use according to any one of example embodiments 99-106, wherein the reduction in pupil size or improvement in visual acuity is maintained for at least 12 hours.

Example embodiment 114: The use according to any one of example embodiments 99-113, wherein the reduction in pupil size or improvement in visual acuity is achieved when the individual is exposed to luminance levels of less than 200 $cd/m^2$.

Example embodiment 115: The use according to any one of example embodiments 99-113, wherein the reduction in pupil size or improvement in visual acuity is achieved when the individual is exposed to luminance levels of less than 150 $cd/m^2$.

Example embodiment 116: The use according to any one of example embodiments 99-113, wherein the reduction in pupil size or improvement in visual acuity is achieved when the individual is exposed to luminance levels of less than 100 $cd/m^2$.

Example embodiment 117: The use according to any one of example embodiments 99-113, wherein the reduction in pupil size or improvement in visual acuity is achieved when the individual is exposed to luminance levels of less than 50 $cd/m^2$.

Example embodiment 118: The use according to any one of example embodiments 99-113, wherein the reduction in pupil size or improvement in visual acuity is achieved when the individual is exposed to luminance levels of less than 10 $cd/m^2$.

Example embodiment 119: The use according to any one of example embodiments 99-113, wherein the reduction in pupil size or improvement in visual acuity is achieved when the individual is exposed to luminance levels of less than 5 $cd/m^2$.

Example embodiment 120: The use according to any one of example embodiments 99-113, wherein the reduction in pupil size or improvement in visual acuity is achieved when the individual is exposed to luminance levels of less than 2 $cd/m^2$.

Example embodiment 121: Use of a compound of Formula I:

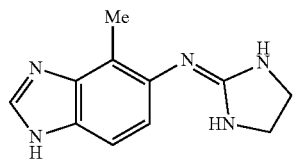

Formula I or a pharmaceutically acceptable salt thereof, in the manufacture of a medicament for the treatment of an ocular condition in an individual in need thereof, wherein the medicament comprises a therapeutically effective amount of the compound of Formula I or a pharmaceutically acceptable salt thereof, and wherein the ocular condition is selected from the group consisting of presbyopia, poor night vision, visual glare, visual starbursts, visual halos, and night myopia.

Example embodiment 122: The use according to example embodiment 121, wherein the ocular condition is presbyopia.

Example embodiment 123: The use according to example embodiment 121, wherein the ocular condition is poor night vision.

Example embodiment 124: The use according to example embodiment 121, wherein the ocular condition is visual glare.

Example embodiment 125: The use according to example embodiment 121, wherein the ocular condition is visual starbursts.

Example embodiment 126: The use according to example embodiment 121, wherein the ocular condition is visual halos.

Example embodiment 127: The use according to example embodiment 121, wherein the ocular condition is night myopia.

Example embodiment 128: The use according to any one of example embodiments 121-127, wherein the medicament, when administered to the individual, is administered to one or both eyes of the individual.

Example embodiment 129: The use according to example embodiment 128, wherein the administration to the eye is topical administration.

Example embodiment 130: The use according to any one of example embodiments 121-129, wherein the medicament, when administered to the individual, is administered to the individual as a pharmaceutically acceptable composition comprising the therapeutically effective amount of the compound of Formula I or a pharmaceutically acceptable salt thereof and a pharmaceutically acceptable excipient.

Example embodiment 131: The use according to example embodiment 130, wherein the pharmaceutically acceptable composition comprises the compound of Formula I in an amount of 0.01% (w/v).

Example embodiment 132: The use according to example embodiment 130, wherein the pharmaceutically acceptable composition comprises the compound of Formula I in an amount of 0.03% (w/v).

Example embodiment 133: The use according to example embodiment 130, wherein the pharmaceutically acceptable composition comprises the compound of Formula I in an amount of 0.1% (w/v).

Example embodiment 134: The use according to example embodiment 130, wherein the pharmaceutically acceptable composition comprises the compound of Formula I in an amount of 0.3% (w/v).

Example embodiment 135: The use according to example embodiment 130, wherein the pharmaceutically acceptable composition is an ocular implant, intracameral implant, intravitreal implant, subconjunctival implant, sub-Tenon's implant, punctum plug, canicular eluting implant, or ocular ring.

Example embodiment 136: The use according to example embodiment 130, wherein the pharmaceutically acceptable composition is a microsphere.

Example embodiment 137: The use according to any one of example embodiments 121-136, wherein the therapeutically effective amount of the compound of Formula I or pharmaceutically acceptable salt thereof in the medicament, when administered to the individual, has binding to the iris pigment that is less than the binding to the iris pigment exhibited by brimonidine.

Example embodiment 138: The use according to any one of example embodiments 121-136, wherein the therapeutically effective amount of the compound of Formula I or pharmaceutically acceptable salt thereof in the medicament is an amount that is less than the amount of brimonidine needed to achieve the same therapeutic effects.

Example embodiment 139: The use according to any one of example embodiments 121-136, wherein the therapeutically effective amount of the compound of Formula I or pharmaceutically acceptable salt thereof in the medicament, when administered to the individual, causes an amount of reduction in pupil size such that the pupil is constricted to a size of between 2 and 3 mm.

Example embodiment 140: The use according to any one of example embodiments 121-136, wherein the therapeutically effective amount of the compound of Formula I or pharmaceutically acceptable salt thereof in the medicament, when administered to the individual, causes an amount of reduction in pupil size such that the pupil is constricted to a size of 3 mm or less.

Example embodiment 141: The use according to any one of example embodiments 121-136, wherein the therapeutically effective amount of the compound of Formula I or pharmaceutically acceptable salt thereof in the medicament, when administered to the individual, causes an amount of reduction in pupil size such that the pupil is constricted to a size of 2.5 mm or less.

Example embodiment 142: The use according to any one of example embodiments 121-136, wherein the therapeutically effective amount of the compound of Formula I or pharmaceutically acceptable salt thereof in the medicament, when administered to the individual, causes an improvement in near visual acuity.

Example embodiment 143: The use according to any one of example embodiments 121-136, wherein the therapeutically effective amount of the compound of Formula I or pharmaceutically acceptable salt thereof in the medicament, when administered to the individual, causes an improvement in intermediate visual acuity.

Example embodiment 144: The use according to any one of example embodiments 121-136, wherein the therapeutically effective amount of the compound of Formula I or pharmaceutically acceptable salt thereof in the medicament, when administered to the individual, causes an improvement in distance visual acuity.

Example embodiment 145: The use according to any one of example embodiments 142-144, where in the improvement in visual acuity is an at least 2-line improvement.

Example embodiment 146: The use according to any one of example embodiments 142-144, where in the improvement in visual acuity is an at least 3-line improvement.

Example embodiment 147: The use according to any one of example embodiments 139-146, wherein the reduction in pupil size or improvement in visual acuity is maintained for at least 1 hour.

Example embodiment 148: The use according to any one of example embodiments 139-146, wherein the reduction in pupil size or improvement in visual acuity is maintained for at least 2 hours.

Example embodiment 149: The use according to any one of example embodiments 139-146, wherein the reduction in pupil size or improvement in visual acuity is maintained for at least 4 hours.

Example embodiment 150: The use according to any one of example embodiments 139-146, wherein the reduction in pupil size or improvement in visual acuity is maintained for at least 6 hours.

Example embodiment 151: The use according to any one of example embodiments 139-146, wherein the reduction in pupil size or improvement in visual acuity is maintained for at least 9 hours.

Example embodiment 152: The use according to any one of example embodiments 139-146, wherein the reduction in pupil size or improvement in visual acuity is maintained for at least 10 hours.

Example embodiment 153: The use according to any one of example embodiments 139-146, wherein the reduction in pupil size or improvement in visual acuity is maintained for at least 12 hours.

Example embodiment 154: The use according to any one of example embodiments 139-153, wherein the reduction in pupil size or improvement in visual acuity is achieved when the individual is exposed to luminance levels of less than 200 $cd/m^2$.

Example embodiment 155: The use according to any one of example embodiments 139-153, wherein the reduction in pupil size or improvement in visual acuity is achieved when the individual is exposed to luminance levels of less than 150 $cd/m^2$.

Example embodiment 156: The use according to any one of example embodiments 139-153, wherein the reduction in pupil size or improvement in visual acuity is achieved when the individual is exposed to luminance levels of less than 100 $cd/m^2$.

Example embodiment 157: The use according to any one of example embodiments 139-153, wherein the reduction in pupil size or improvement in visual acuity is achieved when the individual is exposed to luminance levels of less than 50 $cd/m^2$.

Example embodiment 158: The use according to any one of example embodiments 139-153, wherein the reduction in pupil size or improvement in visual acuity is achieved when the individual is exposed to luminance levels of less than 10 $cd/m^2$.

Example embodiment 159: The use according to any one of example embodiments 139-153, wherein the reduction in pupil size or improvement in visual acuity is achieved when the individual is exposed to luminance levels of less than 5 $cd/m^2$.

Example embodiment 160: The use according to any one of example embodiments 139-153, wherein the reduction in pupil size or improvement in visual acuity is achieved when the individual is exposed to luminance levels of less than 2 $cd/m^2$.

Example embodiment 161: A method of treating an ocular condition selected from the group consisting of presbyopia, poor night vision, visual glare, visual starbursts, visual halos, and night myopia substantially as described herein.

Example embodiment 162: A method of treating an ocular condition selected from the group consisting of presbyopia, poor night vision, visual glare, visual starbursts, visual halos, and night myopia with a compound of Formula I:

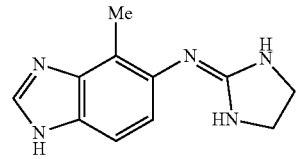 [SMILES: CCc1c(N=C2NCCN2)ccc2[nH]cnc12]

Formula I or a salt thereof substantially as described herein.

Example embodiment 163: A method of using the compound of Formula I:

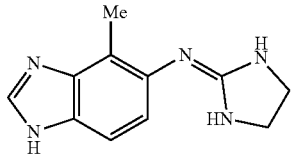 [SMILES: Brc1c(N=C2NCCN2)ccc2[nH]cnc12]

Formula I or a salt thereof substantially as described herein.

DETAILED DESCRIPTION

Figure 1:
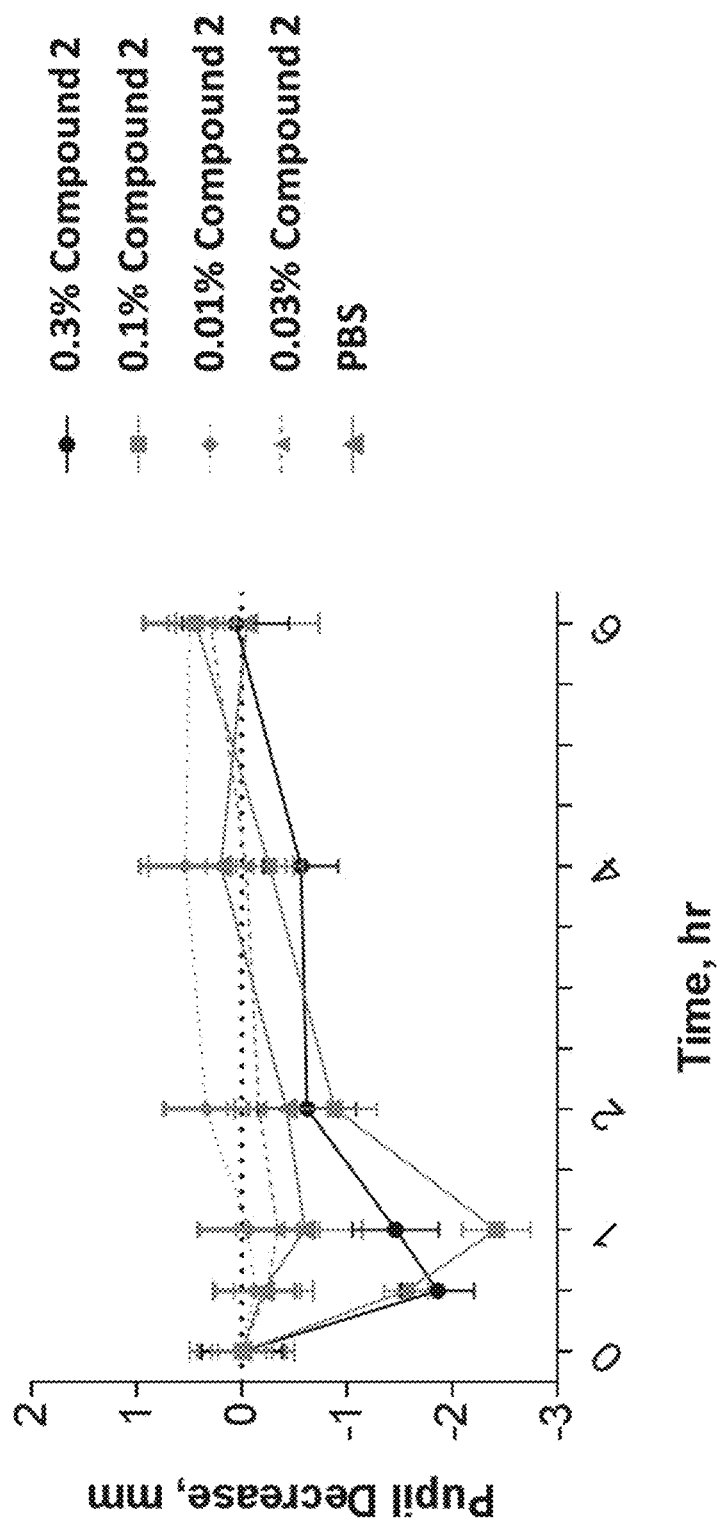
FIG. 1 shows a plot of the dose miotic response curve in Dutch Belted rabbits when topically dosed with compound 2 (see Example 1). Percentage amounts are % w:v.

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning, as are "methyl," "Me," and "$CH_3$". Standard techniques can be used for chemical syntheses, chemical analyses, and formulation.

In some embodiments, compounds described (such as the compound of Formula I) can include pharmaceutically acceptable salt thereof. Such salts can include, for example, acid addition salts, such as hydrochloride, hydrobromide, sulfate, nitrate, phosphorate, acetate, propionate, glycolate, pyruvate, oxalate, malate, malonate, succinate, maleate, fumarate, tartrate, citrate, benzoate, cinnamate, mandelate, methanesulfonate, ethanesulfonate, p-toluene-sulfonate, salicylate and the like, and base addition salts, such as sodium, potassium, calcium, magnesium, lithium, aluminum, zinc, ammonium, ethylenediamine, arginine, piperazine and the like, as well as others identifiable to a skilled person upon a reading of the present disclosure (see, e.g., *Handbook of Pharmaceutical Salts*, P. Heinrich Stahl & Camille G. Wermuth (Eds), Verlag; *Helvetica Chimica Acta*-Zurich, 2002, 329-345; and Berge et al., *Journal of Pharmaceutical Science*, 1977, 66:1-19).

Certain compounds described herein can exist as tautomers which can interconvert between themselves. The structural depiction herein of a particular tautomer should not be construed as limiting the compound to the particular tautomer depicted (even if it may not be the predominant tautomer under a particular set of conditions) unless otherwise indicated.

Unless indicated otherwise herein, the term "about" when used in reference to a value (e.g., weight percentages) is intended to include values proximate to the recited value (and/or range of values) that are equivalent (e.g. bioequivalent) in terms of the functionality of the individual ingredient (e.g. active ingredient or excipient), the composition, or the embodiment. Furthermore, as will be understood by a skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements and that some values and amounts can be rounded up or down such that they would be "about the same" as another value or amount.

The term "therapeutically effective amount" refers to an amount that is effective, when administered to an individual in need of treatment of an ocular condition, such as human or non-human patient, to treat the ocular condition. The extent and/or success of the treatment of the ocular condition when a therapeutically effective amount of a compound and/or composition is administered to an individual would be readily identifiable to a skilled person as is described herein.

Described herein are methods of improving vision in individuals in need thereof, as well as methods of treating ocular conditions in individuals in need thereof. Vision or visual improvement, including but not limited to near, intermediate, and/or distance visual acuity, can for example be reflected in the increase of number of letters correctly read at any time point post dosing, the increase in the average letter change, or 2-line or 3-line (at least) improvement, all from baseline (i.e., from pre-treatment) at different levels of illumination (for example, less than 200 $cd/m^2$, less than 150 $cd/m^2$, less than 100 $cd/m^2$, less than 50 $cd/m^2$, less than 10 $cd/m^2$, less than 5 $cd/m^2$, less than 2 $cd/m^2$, and ranges in between these luminance levels). Night vision improvement can be reflected in visual improvement for patients in dim or dark lighting (e.g., under mesopic or scotopic conditions). Day vision improvement can be reflected in visual improvement for patients in bright lighting as found during daylight hours or in sunshine (e.g., under photopic conditions). Vision improvement using the embodiments described herein can also be achieved in combination with or when using other visual aids and devices (especially those used for treating presbyopia), including but not limited to reading glasses, lens modifying medications, and surgical presbyopic options including intraocular lenses (IOLs).

In some embodiments, the ocular conditions are conditions which can be treated by constricting the size of the pupil. Without wishing to be bound by theory, the inventors believe that by constricting the pupil the "pinhole effect" is achieved which can have therapeutic effects such as improving depth of focus, visual acuity, and other effects of use in treating the ophthalmic conditions such as those described herein. In the pinhole effect, decreasing the pupil diameter increases the depth of focus and decreases the light scattering by blocking some peripheral light rays from entering the eye, thereby preventing unfocused light rays in the periphery from reaching the retina. These actions can help, for example, improve the quality of reading vision in presbyopes and night driving vision for commuters. Thus, conditions treatable by the methods described herein can include, for example, presbyopia, poor night vision, visual glare, visual starbursts, visual halos, and some forms of myopia (e.g. night myopia).

Accordingly, described herein are methods for reducing pupil size for the treatment of an ocular condition in an individual in need of such treatment.

In one embodiment, the method comprises administering to the individual a therapeutically effective amount of a compound of Formula I:

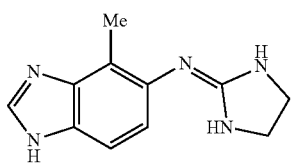 [SMILES: CCc1c(N=C2NCCN2)ccc2[nH]cnc12]

Formula I or a pharmaceutically acceptable salt thereof. The compound of Formula I can be synthesized by methods known to the skilled person (see, for example, U.S. Pat. Nos. 6,495,583 and 5,478,858).

In another embodiment, the ocular condition being treated is selected from the group consisting of presbyopia, poor night vision, visual glare, visual starbursts, visual halos, and some forms of myopia (e.g. night myopia). Thus, described herein is a method of reducing pupil size for the treatment of an ocular condition in an individual in need of such treatment, the method comprising administering to the individual a therapeutically effective amount of a compound of Formula I, or a pharmaceutically acceptable salt thereof, wherein the ocular condition is selected from one or more of the group consisting of presbyopia, poor night vision, visual glare, visual starbursts, visual halos, and some forms of myopia (e.g. night myopia).

In some embodiments, the ocular condition is presbyopia. In other embodiments, the ocular condition is poor night vision. In other embodiments, the ocular condition is visual glare, visual starbursts, visual halos. In other embodiments, the ocular condition is a form of myopia (e.g. night myopia).

In addition, because the compounds described herein are useful for constricting the pupil, they are of use in methods of treating ocular condition such as, for example, presbyopia, poor night vision, visual glare, visual starbursts, visual halos, and some forms of myopia (e.g. night myopia).

Accordingly, described herein are methods of treating ocular condition in an individual in need thereof comprising administering to the individual a therapeutically effective amount of a compound of Formula I, or a pharmaceutically acceptable salt thereof. In some embodiments, the ocular condition is selected from one or more of the group consisting of presbyopia, poor night vision, visual glare, visual starbursts, visual halos, and some forms of myopia (e.g. night myopia).

In some embodiments of the methods described herein, the compound of Formula I, or a pharmaceutically acceptable salt thereof, can be administered directly to one or both of the eyes of the individual. In some embodiments, the compound of Formula I can be administered to both eyes. In other embodiments, the compound of Formula I can be administered to only one of the eyes.

In some embodiments of the methods described herein where the compound of Formula I is administered directly to one or both eyes of the individual, the administration can be done topically the eye.

Additionally, in some embodiments of the methods described herein, the compound of Formula I, or a pharmaceutically acceptable salt thereof, can be administered as a pharmaceutically acceptable composition comprising the compound of Formula I, or a pharmaceutically acceptable salt thereof. Such a composition can be administered to one or both eyes of the individual by various route of administration (for example, topically).

The inventors have surprisingly found the compound of Formula I has greater in vivo activity than would have been predicted based in the in vitro activity of the compound of Formula I when compared to similar alpha-2-adrenergic receptor agonists, which can result in a greater duration of therapeutic activity of the compound of Formula I when compared to other alpha-2-adrenergic receptor agonists. Thus, in some embodiments, the therapeutically effective amount of the compound of Formula I is an amount which, when administered to the individual, results in an increased efficacy and/or duration of effect when compared to other alpha-2-adrenergic receptor agonists (for example, brimonidine).

In particular, one effect of interest can be a reduction in pupil size (pupil constriction) when the compound of Formula I is administered to an individual. Thus, in some embodiments, a particular therapeutically effective amount of the compound of Formula I, when administered to an individual, can cause an amount of reduction in pupil size such that the pupil is constricted to a size of 3 mm or less, and in particular to a size of between 2 and 3 mm, from a natural baseline size which is larger than 3 mm. As would be apparent to a person skilled in the art, the natural baseline size of the pupil can depend on the particular lighting conditions/luminance levels (for example, less than 200 $cd/m^2$, less than 150 $cd/m^2$, less than 100 $cd/m^2$, less than 50 $cd/m^2$, less than 10 $cd/m^2$, less than 5 $cd/m^2$, less than 2 $cd/m^2$, and ranges in between these luminance levels) and age of the patient. Thus, baseline pupil sizes can range from about 6 to about 7 mm in low light to about 3 to about 4 mm in bright light, and in some embodiments, the therapeutically effective amount of the compound of Formula I can be an amount that reduces the pupil size from these baseline sizes to a size of 3 mm or less, and in particular to a size of between 2 and 3 mm. In some embodiments, these reductions in pupil size from baseline sizes can be achieved when the individual is exposed to luminance levels of, for example, less than 200 cd/m$^2$, less than 150 cd/m$^2$, less than 100 cd/m$^2$, less than 50 cd/m$^2$, less than 10 cd/m$^2$, less than 5 cd/m$^2$, less than 2 cd/m$^2$, and ranges in between these luminance levels.

A reduction of pupil size to a size of 3 mm or less, and in particular to a size of between 2 to 3 mm, can, for example, improve the at near reading ability of presbyopes, in particular at lower light conditions (see, e.g. Xu et al. "The effect of light level and small pupils on presbyopic reading performance." *Investigative ophthalmology & visual science* 57, no. 13 (2016): 5656-5664.) However, brimonidine decreases pupil size to average 3.4 mm in presbyopic patients at different lighting conditions (see e.g. McDonald II et al. "Effect of brimonidine tartrate ophthalmic solution 0.2% on pupil size in normal eyes under different luminance conditions." *Journal of Cataract & Refractive Surgery* 27, no. 4 (2001): 560-564.), and thus is not ideal to improve depth of focus and improve reading acuity. The compound of Formula I has both a greater peak drop and longer duration of a pupil size being between 2 mm and 3 mm for a period of time between at least about 1 hour to at least about 9 hours while such durations of pupil constriction to 2-3 mm range are not seen when another alpha-2-adrenergic receptor agonist such as brimonidine is administered.

Thus, in some embodiments, a particular therapeutically effective amount of the compound of Formula I, when administered to an individual, can have a duration of reduction in pupil size where the pupil is constricted to a size of 3 mm or less, and in particular to a size of between 2 and 3 mm for at least 1 hour, for at least 2 hours, for at least 4 hours, for at least 6 hours, or for at least 9 hours, for at least 10 hours, for at least 12 hours, and for ranges in between those times. In some embodiments, these pupil size reductions can be achieved when the individual is exposed to luminance levels of, for example, less than 200 cd/m$^2$, less than 150 cd/m$^2$, less than 100 cd/m$^2$, less than 50 cd/m$^2$, less than 10 cd/m$^2$, less than 5 cd/m$^2$, less than 2 cd/m$^2$, and ranges in between these luminance levels.

In other embodiments, a particular therapeutically effective amount of the compound of Formula I, when administered to an individual, can have a duration of reduction in pupil size where the pupil is constricted to a size of about 2.0 mm for at least 1 hour, for at least 2 hours, for at least 4 hours, for at least 6 hours, for at least 9 hours, for at least 10 hours, or for at least 12 hours, and for ranges in between those times. In other embodiments, a particular therapeutically effective amount of the compound of Formula I, when administered to an individual, can have a duration of pupil constriction where the pupil is constricted to a size of about 2.5 mm for at least 1 hour, for at least 2 hours, for at least 4 hours, for at least 6 hours, for at least 9 hours, for at least 10 hours, or for at least 12 hours and for ranges in between those times.

The inventors have also surprisingly found that, unlike the marketed alpha-2-adrenergic receptor agonist brimonidine (which has elevated binding to iris melanin pigments), the compound of Formula I does not exhibit much binding to iris melanin pigments. Thus, the compound of Formula I can be administered with more consistent dosing between individuals having different eye colors/iris pigmentation.

Thus, in some embodiments, the therapeutically effective amount of the compound of Formula I is an amount which, when administered to the individual, results in reduced amount of binding to the iris pigment of the individual when compared to the administration of about the same amount of another alpha-2-adrenergic receptor agonist (for example, brimonidine). For example, in some embodiments, a particular therapeutically effective amount of the compound of Formula I, when administered to an individual, can result in binding to the iris pigment that is about 8 to about 10 times less than the binding to the iris pigment when about the same amount of brimonidine is administered to the individual, especially when the individual has an iris which would be considered a dark iris (see, e.g. Franssen, L.; Coppens, J. E.; van den Berg, T. J., Grading of iris color with an extended photographic reference set. *Journal of optometry* 2008, 1 (1), 36-40).

Furthermore, this reduced amount of binding to iris pigments can result in reduced amount of compound of Formula I needed to achieve a particular therapeutic effect than would be needed if brimonidine were used, especially when the individual has an iris which would be considered a dark iris. Thus, in some embodiments, the amount of compound of Formula I needed would be about 30 to about 100 times less than the amount of brimonidine needed to achieve similar therapeutic effects as brimonidine (e.g. pupil constriction). In some embodiments, the amount of compound of Formula I needed would be about 30 times, about 40 times, about 50 times, about 60 times, about 70 times, about 80 times, about 90 times, or about 100 times less than the amount of brimonidine needed to achieve similar therapeutic effects as brimonidine (e.g. pupil constriction).

In addition, due to the reduced amount of the compound of Formula I needed, it is anticipated that the lower potential compound of Formula I needed would result in reduced incidence of side effects normally associated with alpha-2-adrenergic receptor agonists (e.g. sedation). In addition, without wishing to be bound by theory, the reduced binding of the compound of Formula I to iris pigments can lead to an amount of the compound of Formula I having the increased duration time of the therapeutic benefit when compared to an equivalent amount of an alpha adrenergic receptor agonist such as brimonidine, especially when the individual has an iris which would be considered a dark iris.

In some embodiments of the methods described herein, the ocular condition being treated is presbyopia. Presbyopia is an age-related condition that affects nearly 1.7 billion people. In presbyopes, the ability of the eye to focus on near objects (accommodation) decreases with age and is believed to be caused by hardening of the lens of the eye on an individual as they age.

The extent and/or success of the treatment of presbyopia in an individual in need thereof can be determined by methods known to those skilled in the art (e.g. physicians and other medical workers). For example, an improvement in the uncorrected near visual acuity, intermediate visual acuity, and/or distance visual acuity when the compound of Formula I is administered relative to the visual acuity when the compound is not administered. The improvement can be quantitatively measured by measuring the improvement in the number of lines correctly read by the patient on eye charts identifiable to those skilled in the art. For example, an individual can correctly read one or more (for example, two, three, or four) lines when the compound of Formula I is administered to the individual than the number of lines the individual can correctly read prior to the administration of the compound of Formula I. The improvement can be measured in one or both eyes, and under normal or low light conditions (for example, less than 200 cd/m$^2$, less than 150 cd/m², less than 100 cd/m², less than 50 cd/m², less than 10 cd/m², less than 5 cd/m², less than 2 cd/m², and ranges in between these luminance levels). In addition, non-quantitative (i.e. qualitative) measurements of the extend and/or success of the treatments can be measured, such as the individual's self-reporting of the improvement of the individual's vision after administration of the compound of Formula I. For example, an individual might report improved reading ability and/or the lack of need for reading glasses after the administration of the compound of Formula I. Additionally, an individual might also report reduced headaches and eye strain (which is normally present in the individual when the presbyopia is not being treated by other means such as reading glasses) when the individual is administered the compound of Formula I.

Another measurement of the extent and/or success of the treatment of presbyopia in an individual in need thereof can be the measurement of the improvement in depth of focus (the distance, which can be measured in diopters or other units identifiable to a skilled person, that a viewed object can be moved away from and towards the individual before focus is lost) in an individual when the compound of Formula I is administered to the individual relative to the depth of focus in the individual prior to the administration of the compound of Formula I. The depth of focus can be measured and determined by methods identifiable to those skilled in the art, such as, for example, wavefront aberrometry and other methods identifiable to a skilled person.

Another measurement of the extent and/or success of the treatment of presbyopia in an individual in need thereof can be the measurement of pupil diameter and appearance in an individual when the compound of Formula I is administered to the individual relative to the pupil diameter and appearance in the individual prior to the administration of the compound of Formula I. The measurement of the pupil diameter and appearance can be measured by methods identifiable to a skilled person (e.g. using a wavefront aberrometer) under various lighting conditions identifiable to a skilled person so as to reflect nighttime outdoor and traffic lighting scenarios.

Another measurement of the extent and/or success of the treatment of presbyopia in an individual in need thereof can be the measurement of the change in visual field of an individual when the compound of Formula I is administered to the individual relative to the visual field of the individual prior to the administration of the compound of Formula I. The determination of an individual's visual field can be done by methods identifiable to a skilled person. For example, the individual can cover one eye while fixating on the eye of an examiner with the uncovered eye. The individual can then be asked to indicate the number of fingers briefly flashed by the examiner in each of the four quadrants (left, right, up, and down).

In some embodiments of the methods described herein, the ocular condition being treated is poor night vision. Many individuals suffer from poor night vision which is a condition in which an individual has impaired vision under low light conditions such as those occurring at night. The causes of the poor night vision can include corneal or lenticular aberrations which can be natural, but they can also result from ocular interventions such as laser surgery (e.g. LASIK). Without wishing to be bound by theory, the inventors believe that poor night vision can result when the pupil dilates under low light conditions which, for example if there are corneal or lenticular aberrations, can lead to some light rays not focusing on the pupil and that therefore improvement in night vision can be achieved if the pupil is constricted (e.g. by administering the compound of Formula I to an individual with poor night vision).

The extent and/or success of the treatment of poor night vision in an individual in need thereof can be determined by methods known to those skilled in the art (e.g. physicians and other medical workers). For example, one measurement of the extent and/or success of the treatment of poor night vision in an individual can be an improvement in mesopic contrast sensitivity (with or without glare) as measured by systems identifiable to a skilled person (such as the Holladay Automated Contrast Sensitivity System, or HACSS™) when the compound of Formula I is administered relative to the mesopic contrast sensitivity when the compound is not administered.

Another measurement of the extent and/or success of the treatment can be, for example, an improvement in the uncorrected near distance visual acuity, intermediate distance acuity, and/or distance acuity (all of which can be low contrast acuity or high contrast acuity; see for example Edwards, J. D.; Burka, J. M.; Bower, K. S.; Stutzman, R. D.; Sediq, D. A.; Rabin, J. C., Effect of brimonidine tartrate 0.15% on night-vision difficulty and contrast testing after refractive surgery. *Journal of Cataract & Refractive Surgery* 2008, 34 (9), 1538-1541) under low light conditions when the compound of Formula I is administered relative to the visual acuity when the compound is not administered. The improvement can be quantitatively measured by measuring the improvement in the number of lines correctly read by the patient under low light conditions on eye charts identifiable to those skilled in the art. For example, an individual can correctly read one or more (for example, two, three, or four) lines under low light conditions when the compound of Formula I is administered to the individual than the number of lines the individual can correctly read prior to the administration of the compound of Formula I. The improvement can be measured in one or both eyes.

In addition, non-quantitative (i.e. qualitative) measurements of the extend and/or success of the treatments can be measured, such as the individual's self-reporting of the improvement of the individual's vision under low light conditions after administration of the compound of Formula I. For example, an individual might report improved night vision (e.g. while driving) and/or the lack of need for reading glasses under low light condition (e.g. at a restaurant with low lighting conditions) after the administration of the compound of Formula I.

In some embodiments of the methods described herein, the ocular condition being treated is visual glare. Visual glare is a side effect of some ophthalmic surgeries such as laser surgery (e.g. LASIK) characterized by visual aberrations generally seen at night in which light enters the eye and interferes with vision. Without wishing to be bound by theory, the inventors believe that the visual aberrations seen in visual glare under low light conditions are caused and/or exacerbated by the additional light that enters the eye when the pupil dilates and can therefore be treated by constricting the pupil by administering the compound of Formula I to a person experiencing visual glare.

In some embodiments of the methods described herein, the ocular condition being treated is visual starbursts. Visual starbursts are visual disturbances (which can be a side effect of some ophthalmic surgeries such as LASIK) in which light sources (such as street lamps and car headlights) appear to emit light in a starburst pattern emanating from the source of the light and which in some cases can obscure objects in close proximity to the light source, such as a pedestrian or cyclist that is near a headlight (see, e.g. the web page lasikcomplications.com/starbursting.htm). In other embodiments of the methods described herein, the ocular condition being treated is visual halos. Visual halos are another visual disturbance (which can be a side effect of some ophthalmic surgeries such as LASIK) that take the form of diffuse rings that can be seen around light sources, such street lamps, headlights, and illuminated reflective street signs (see, e.g. the web pages lasikcomplications.com/halos.htm and londonvisionclinic.com/post-lasik-patients-risk-of-halos-and-starbursts-around-bright-lights-at-night).

The extent and/or success of the treatment of visual glare, visual starbursts, and/or visual halos in an individual in need thereof can be determined by methods known to those skilled in the art (e.g. physicians and other medical workers). For example, the extent of the treatment can be determined by using tests known to a skilled person to assess the extent of visual glare, visual starbursts, and/or visual halos before and after having the compound of Formula I administered to them. For example, the severity of the visual glare, visual starbursts, and/or halos seen by an individual can be measured before administration of the compound of Formula I and compared to the severity of the visual glare, visual starbursts, and/or halos seen by the individual after administration of the compound of Formula I. The measurements can be qualitative (e.g. based on a questionnaire) or quantitative (e.g. by having the individual measure the size of a starburst and/or halo on a computerized optical system that can generate halos and starbursts) depending on the particular test used, which would be identifiable to a skilled person (see, e.g., Lee, J. H.; You, Y. S.; Choe, C. M.; Lee, E. S., Efficacy of brimonidine tartrate 0.2% ophthalmic solution in reducing halos after laser in situ keratomileusis. *Journal of Cataract & Refractive Surgery* 2008, 34 (6), 963-967 and Xu, R.; Kollbaum, P.; Thibos, L.; Lopez-Gil, N.; Bradley, A., Reducing starbursts in highly aberrated eyes with pupil miosis. *Ophthalmic and Physiological Optics* 2018, 38 (1), 26-36; and Hunkeler, J. D.; Coffman, T. M.; Paugh, J.; Lang, A.; Smith, P.; Tarantino, N., Characterization of visual phenomena with the Array multifocal intraocular lens. *Journal of Cataract & Refractive Surgery* 2002, 28 (7), 1195-1204). In addition, the extent of the treatment can also be self-reported by a patient after the patient has been administered the compound of Formula I and has been able to drive at night while under its therapeutic effect.

In some embodiments of the methods described herein, the ocular condition being treated is a form of myopia (e.g. night myopia). For example, night myopia is a type of myopia (i.e. "nearsightedness", of the inability to focus on distant objects) which tends to manifest itself at night and/or under low light conditions. Without wishing to be bound by theory, the inventors believe that night myopia can be caused by additional unfocused light rays entering the eye when the pupil is dilated under the lower light conditions and can thus be treated by reducing the size of the pupil by administering the compound of Formula I to a person suffering from night myopia.

The extent and/or success of the treatment of night myopia in an individual in need thereof can be determined by methods known to those skilled in the art (e.g. physicians and other medical workers). For example, one measurement of the extent and/or success of the treatment can be, for example, an improvement in the intermediate distance acuity and/or distance acuity under low light conditions when the compound of Formula I is administered relative to the visual acuity when the compound is not administered. The improvement can be quantitatively measured by measuring the improvement in the number of lines correctly read by the patient under low light conditions on eye charts identifiable to those skilled in the art. For example, an individual can correctly read one or more (for example, two, three, or four) lines under low light conditions when the compound of Formula I is administered to the individual than the number of lines the individual can correctly read prior to the administration of the compound of Formula I. The improvement can be measured in one or both eyes.

In addition, non-quantitative (i.e. qualitative) measurements of the extend and/or success of the treatments can be measured, such as the individual's self-reporting of the improvement of the individual's vision under low light conditions after administration of the compound of Formula I. For example, an individual might report improved night distance vision (e.g. while driving) after the administration of the compound of Formula I.

While the duration of the treatment of the ocular conditions (e.g. the amount of time vision is improved) may not be permanent, and may vary from individual to individual, the compound of Formula I can be administered in such a way so as to prolong the treatment of the presbyopia. For example, depending on the duration of the vision-improving effects of a particular dose of the compound of Formula I (which can be determined by a skilled person such as a physician), the compound can be administered once a day, twice a day, three times a day, four times a day, or with any other frequency as can be determined by a skilled person such as a physician.

In some embodiments, the pharmaceutically acceptable composition is in the form of a solution suitable for ophthalmic application. In one embodiment, the solution is prepared using a physiological saline solution as a major vehicle. The pH of such ophthalmic solutions should for example be maintained from 4.5 to 8.0 with an appropriate buffer system, a neutral pH being preferred but not essential. Various buffers and means for adjusting pH can be used so long as the resulting preparation is ophthalmically acceptable. Accordingly, buffers include, but are not limited to, acetate buffers, citrate buffers, phosphate buffers and borate buffers. Acids or bases can be used to adjust the pH of these formulations as needed.

The formulations can also contain conventional, pharmaceutically acceptable preservatives, stabilizers and surfactants. Exemplary preservatives that can be used in the pharmaceutical compositions include, but are not limited to, benzalkonium chloride, thimerosal, phenylmercuric acetate, phenylmercuric nitrate, chlorobutanol, methyl paraben, propyl paraben, phenylethyl alcohol, edetate disodium, ascorbic acid, polydronium chloride (e.g. ONAMER® M), stabilized oxychloro complex/stabilized chlorine dioxide (e.g. PURITE®), and other agents known to those skilled in the art. In ophthalmic products, typically such preservatives are employed at a level of from 0.004% to 0.02%. Stabilizers include, but are not limited to, polyvinyl alcohol, povidone, hydroxypropyl methyl cellulose, poloxamers, carboxymethyl cellulose, and hydroxyethyl cellulose cyclodextrin. In addition, the formulations can also be devoid of preservatives. Such formulations devoid of preservatives are said to be "preservative-free."

The ophthalmic solution preparation can also include a surfactant. Surfactants are useful to assist in dissolving an excipient or an active agent, dispersing a solid or liquid in a composition, enhancing wetting, modifying drop size, etc. Useful surfactants include, but are not limited to surfactants of the following classes: alcohols; amine oxides; block polymers; carboxylated alcohol or alkylphenol ethoxylates; carboxylic acids/fatty acids; ethoxylated alcohols; ethoxylated alkylphenols; ethoxylated aryl phenols; ethoxylated fatty acids; ethoxylated; fatty esters or oils (animal and/or vegetable); fatty esters; fatty acid methyl ester ethoxylates; glycerol esters; glycol esters; lanolin-based derivatives; lecithin and lecithin derivatives; lignin and lignin derivatives; methyl esters; monoglycerides and derivatives; polyethylene glycols; polymeric surfactants; propoxylated and ethoxylated fatty acids, alcohols, or alkyl phenols; protein-based surfactants; sarcosine derivatives; sorbitan derivatives; sucrose and glucose esters and derivatives.

Tonicity adjustors can be added as needed or convenient. They include, but are not limited to, salts, particularly sodium chloride, potassium chloride, mannitol, erythritol, carnitine, and glycerin, or any other suitable ophthalmically acceptable tonicity adjustor.

An ophthalmically acceptable antioxidant can be included, and examples include sodium metabisulfite, sodium thiosulfate, acetylcysteine, butylated hydroxyanisole and butylated hydroxytoluene.

Other excipient components which can be included in the ophthalmic preparations are chelating agents. An exemplary chelating agent is edetate disodium, although other chelating agents are known and suitable, alone or in combination with edetate disodium.

The pharmaceutically acceptable composition (also referred to herein as a preparation) can comprise the compound of Formula I in an amount between about 0.01% and about 1% (w/v), or between about 0.01% and about 0.2% (w/v), about 0.01% and about 0.3% (w/v), about 0.01% and about 0.4% (w/v), about 0.01% and about 0.5% (w/v), about 0.01% and about 0.5% (w/v), about 0.01% and about 0.6% (w/v), about 0.01% and about 0.7% (w/v), about 0.01% and about 0.8% (w/v), or about 0.01% and about 0.9% (w/v), and ranges in between any of these selected amounts of the compound of Formula I.

The pharmaceutically acceptable composition can also comprise the compound of Formula I in an amount between about 0.01% and about 0.02% (w/v), between about 0.02% and about 0.03% (w/v), between about 0.03% and about 0.04% (w/v), between about 0.04% and about 0.05% (w/v), between about 0.05% and about 0.06% (w/v), between about 0.06% and about 0.06% (w/v), between about 0.06% and about 0.07% (w/v), between about 0.07% and about 0.08% (w/v), between about 0.08% and about 0.09% (w/v), between about 0.09% and about 0.10% (w/v), and ranges in between any of these selected amounts of the compound of Formula I.

The pharmaceutically acceptable composition can also comprise the compound of Formula I in an amount between about 0.01% and about 0.06% (w/v), between about 0.06% and about 0.11% (w/v), between about 0.11% and about 0.16% (w/v), between about 0.16% and about 0.21% (w/v), between about 0.21% and about 0.26% (w/v), between about 0.26% and about 0.31% (w/v), between about 0.31% and about 0.36% (w/v), between about 0.36% and about 0.41% (w/v), between about 0.41% and about 0.46% (w/v), between about 0.46% and about 0.51% (w/v), between about 0.51% and about 0.55% (w/v), between about 0.55% and about 0.60% (w/v), between about 0.60% and about 0.65% (w/v), between about 0.65% and about 0.70% (w/v), between about 0.70% and about 0.75% (w/v), between about 0.75% and about 0.80% (w/v), between about 0.80% and about 0.85% (w/v), between about 0.85% and about 0.90% (w/v), between about 0.90% and about 0.95% (w/v), or between about 0.95% and about 1.00% (w/v), and ranges in between any of these selected amounts of the compound of Formula I.

In addition, the pharmaceutically acceptable composition can comprise the compound of Formula I in an amount between about 0.001% and about 1% (w/v), or between about 0.001% and about 0.2% (w/v), about 0.001% and about 0.3% (w/v), about 0.001% and about 0.4% (w/v), about 0.001% and about 0.5% (w/v), about 0.001% and about 0.6% (w/v), about 0.001% and about 0.7% (w/v), about 0.001% and about 0.8% (w/v), or about 0.001% and about 0.9% (w/v), and ranges in between any of these selected amounts of the compound of Formula I.

The pharmaceutically acceptable composition can also comprise the compound of Formula I in an amount between about 0.001% and about 0.01% (w/v), about 0.001% and about 0.02% (w/v), about 0.001% and about 0.03% (w/v), about 0.001% and about 0.04% (w/v), about 0.001% and about 0.05% (w/v), about 0.001% and about 0.06% (w/v), about 0.001% and about 0.07% (w/v), about 0.001% and about 0.08% (w/v), or about 0.001% and about 0.09% (w/v), about 0.001% and about 0.01%, and ranges in between any of these selected amounts of the compound of Formula I.

The pharmaceutically acceptable composition can also comprise the compound of Formula I in an amount between about 0.001% and about 0.002% (w/v), between about 0.002% and about 0.003% (w/v), between about 0.003% and about 0.004% (w/v), between about 0.004% and about 0.005% (w/v), between about 0.005% and about 0.006% (w/v), between about 0.006% and about 0.006% (w/v), between about 0.006% and about 0.007% (w/v), between about 0.007% and about 0.008% (w/v), between about 0.008% and about 0.009% (w/v), between about 0.009% and about 0.010% (w/v), and ranges in between any of these selected amounts of the compound of Formula I.

In addition, the pharmaceutically acceptable composition can comprise the compound of Formula I in an amount between about 0.003% and about 1% (w/v), or between about 0.003% and about 0.2% (w/v), about 0.003% and about 0.3% (w/v), about 0.003% and about 0.4% (w/v), about 0.003% and about 0.5% (w/v), about 0.003% and about 0.5% (w/v), about 0.003% and about 0.6% (w/v), about 0.003% and about 0.7% (w/v), about 0.003% and about 0.8% (w/v), or about 0.003% and about 0.9% (w/v), and ranges in between any of these selected amounts of the compound of Formula I.

The pharmaceutically acceptable composition can also comprise the compound of Formula I in an amount between about 0.003% and about 0.01% (w/v), about 0.003% and about 0.02% (w/v), about 0.003% and about 0.03% (w/v), about 0.003% and about 0.04% (w/v), about 0.003% and about 0.05% (w/v), about 0.003% and about 0.06% (w/v), about 0.003% and about 0.07% (w/v), about 0.003% and about 0.08% (w/v), about 0.003% and about 0.09% (w/v), or about 0.003% and about 0.01%, and ranges in between any of these selected amounts of the compound of Formula I.

In addition, the pharmaceutically acceptable composition can also comprise the compound of Formula I in an amount between about 0.1% and about 0.2% (w/v), about 0.2% and about 0.3% (w/v), about 0.3% and about 0.4% (w/v), about 0.4% and about 0.5% (w/v), about 0.5% and about 0.6% (w/v), about 0.6% and about 0.7% (w/v), about 0.7% and about 0.8% (w/v), about 0.8% and about 0.9% (w/v), or about 0.9% and about 1% (w/v), and ranges in between any of these selected amounts of the compound of Formula I. Additional amounts of the compound of Formula I for the compositions described herein would be identifiable to a skilled person upon a reading of the present disclosure.

In addition, the pharmaceutically acceptable composition can also comprise the compound of Formula I in an amount between about 0.01% and about 0.02% (w/v), about 0.02% and about 0.03% (w/v), about 0.03% and about 0.04% (w/v), about 0.04% and about 0.05% (w/v), about 0.05% and about 0.06% (w/v), about 0.06% and about 0.07% (w/v), about 0.07% and about 0.08% (w/v), about 0.08% and about 0.09% (w/v), or about 0.09% and about 0.1% (w/v), and ranges in between any of these selected amounts of the compound of Formula I. Additional amounts of the compound of Formula I for the compositions described herein would be identifiable to a skilled person upon a reading of the present disclosure.

In addition, the pharmaceutically acceptable composition can comprise the compound of Formula I in an amount of about 0.01% (w/v), about 0.03% (w/v), about 0.1% (w/v), or about 0.3% (w/v), and other amounts other than these selected amounts of the compound of Formula I. Additional amounts of the compound of Formula I for the compositions described herein would be identifiable to a skilled person upon a reading of the present disclosure.

In some embodiments, when the compound of Formula I is part of a pharmaceutically acceptable composition, the compound is the only active ingredient which have therapeutic activity such that would be of use for the treatment or control of ocular conditions (e.g. presbyopia, poor night vision, visual glare, visual starbursts, visual halos, and some forms of myopia (e.g. night myopia)). The term "active ingredient" as used herein refers to a component of a pharmaceutically acceptable composition which is responsible for the therapeutic effect of composition, whereas the other components of the composition (e.g. excipients, carriers, and diluents) are not responsible for the therapeutic effect of composition, even if they have other functions in the composition which are necessary or desired as part of the formulation (such as lubrication, flavoring, pH control, emulsification, stabilization, preservation, and other functions other than the therapeutic effect of composition as described herein). In particular, in some embodiments, pharmaceutically acceptable compositions described herein in which the compound of Formula I is the only active ingredient which has therapeutic activity are compositions in which there are no other components which would be considered to have therapeutic activity for the treatment or control of ocular conditions (e.g. presbyopia, poor night vision, visual glare, visual starbursts, visual halos, and some forms of myopia (e.g. night myopia)).

The ophthalmic formulation, in another embodiment, can be packaged in a form suitable for metered application, such as in a container equipped with a dropper, to facilitate application to the eye. Containers suitable for drop wise application are usually made of suitable inert, non-toxic plastic material, and generally contain between about 0.5 and about 15 ml solution. One package can contain one or more unit doses. Preservative-free solutions are often formulated in non-resealable containers containing up to about ten, such as up to about five units doses, where a typical unit dose is from one to about 8 drops, such as from one to about 3 drops. The volume of one drop usually is about 20-35 µL. In some embodiments, the containers can be multidose preservative-free (MDPF) containers (see, e.g. Chapter 20 of Ong, S. et al. *Drug Development-A Case Study Based Insight into Modern Strategies* 2011).

In addition, in some embodiments, various ocular delivery methods for administration to the eye are also contemplated for the compositions and/or compounds (e.g. compound of Formula I) described herein. For example, ocular administration methods can include, for example, intravitreal administration, intracameral administration, and subconjunctival administration, and other ocular administration methods identifiable to a skilled person. In addition, additional administration methods such as using ocular drug delivery systems (e.g. ocular implants, intracameral implants, intravitreal implants, subconjunctival implants, sub-Tenon's implants, punctum plugs, canicular eluting implants, and ocular rings) are also envisioned for delivering the compounds and/or compositions described herein (for example, for sustained release over periods of days, weeks, or other periods recommended by a physician), as are injectable sustained-release formulations resulting in a depot, such as the compound of Formula I in a PLGA-based microsphere, which can also be used in any of the intraocular compartments such as the subconjunctiva, sub-Tenon's, intracameral, and intravitreal spaces (see, e.g., Kuno *Polymers* 2011, 3, 193-221; U.S. Pat. Nos. 9,289,413 and 9,504,653; US patent application publications 2011/0182966, 2016/0022695, and 2016/0296532; and Chee, S.-P., *Journal of Ocular Pharmacology and Therapeutics* 2012, 28 (4), 340-349 and Tejpal, Y., et al., *J Drug Deliv. Therap.* 2013, 3, 114-123).

Also contemplated is a kit comprised of an ocular preparation comprising the compound of Formula I and instructions for administering the preparation to the eye. The ocular preparation is, in one embodiment, provided or packaged in multidose form. In this embodiment, the preparation preferably comprises the compound of Formula I and a pharmaceutically acceptable excipient. Any of the excipients discussed herein are suitable for the ocular preparation. In one embodiment, the preparation comprises a preservative that prevents microbial contamination during use (i.e., repeated use).

The instructions for administration typically provide dosing instructions. In various embodiments, the instructions can be to administer the preparation once per day, twice per day or three times per day. In embodiments where the preparation is a liquid preparation, the administration can be to place one drop, two drops, three drops, or more in the eye or in both eyes (e.g., if one eye is affected by the ocular condition, both eyes can be treated, or if both eyes are affected by the condition) once per day, twice per day, three times per day, or more.

EXAMPLES

The following examples are intended only to illustrate the methods of the present disclosure and should in no way be construed as limiting the methods of the present disclosure.

Example 1

In Vitro Activity of Alpha Adrenergic Receptor Agonists

An in vitro FLIPR (fluorometric image plate reader) assay was performed on several compounds, including the compound of Formula I (entry 1 in Table 1).

Specifically, four HEK293 stable cell lines were used in the FLIPR assay. The HEK293 cell line which stably expressed the bovine alpha adrenergic 1A receptor was used to characterize the alpha1 pharmacology. The alpha-2 adrenergic receptor family is a G coupled G-protein receptor. Therefore, in order to use these cell lines in the calcium based FLIPR assay, the chimeric G-protein Gqi5 was used to force the coupling of the human alpha-2A, alpha-2B, and alpha-2C receptors to the calcium pathway. Cells were plated, in triplicate, in poly-D-lysine coated 384-well plates at 25,000 cells per well and grown overnight in DMEM supplemented with 10% fetal bovine serum. For FLIPR evaluation, cells were washed twice with HBSS/HEPES buffer (1X Hanks Buffered Salt Solution, 20 mM HEPES, pH 7.4) prior to the addition of Fluo-4-AM (4 uM Fluo-4-AM, 0.04% pluronic acid in HBSS/HEPES buffer), a calcium-sensitive dye. Cells were loaded with dye for 40 minutes at 37° C., and then washed 4 times with HBSS/HEPES buffer to remove the excess dye. The test compounds were profiled at concentrations between 0.64 nM and 10,000 nM using a four-fold dilution factor. Norepinephrine was used as the standard full agonist for evaluating the alpha-1 receptor relative efficacy and Brimonidine (Compound 4) was used as the standard full agonist for evaluating the alpha-2 receptor relative efficacy. Either norepinephrine or brimonidine was tested at concentrations between 0.064 nM and 1000 nM using a four-fold dilution factor.

The receptor activation was initiated by the addition of the appropriate dilutions of compounds and the transient calcium signal was captured. The peak height of the calcium curve was determined and utilized for calculation of $EC_{50}$ and relative efficacy values using Activity Base software. $EC_{50}$ was calculated using a 4 Parameter Logistic Equation: $y=A+((B-A)/(1+((C/x)\string^AD)))$ where A and B represents the bottom and top plateau of the curve; C represents the $EC_{50}$ value; D represents the slope factor; and x and y represent the original x (drug concentration) and y (fluorescence signal, RFU) values.

TABLE 1

| Compound | Structure | bovine alpha1A $EC_{50}$ (nm) | human alpha2A $EC_{50}$ (nm) |
|---|---|---|---|
| 1 | Me ... (Formula I) | 286 | 0.7 |
| 2 | Et ... | 1651 | 11 |
| 3 | Br ... | 1000 | 1.0 |
| 4 | Br ... (brimonidine) | 1205 | 0.8 |

Based on the in vitro pharmacology, it would have been expected that alpha-2-adrenergic receptor pan-agonists such as compounds 2 and 3 and the compound of Formula I (compound 1) would have similar miotic efficacy (peak and duration) in rabbit like brimonidine (compound 4). However, the compound of Formula I was found to have unexpected superior properties in vivo as is shown in the next example.

Example 2

In Vivo Rabbit Miosis Model

Female Dutch Belted rabbits (Covance, Princeton, N.J.) weighing between 2-4 kg were used for these studies. All experimental animals received the selected form of the compound of Formula I (compound 1), compound 2, brimonidine (compound 4), or vehicle in in a single unilateral topical dose in the right eye. For topical dosing, eye drops (volume=35 μl) were instilled into the lower conjunctival sac of the test eye.

Pupil diameter was measured in both the treated and untreated eye with an Optistick to the nearest 0.5 mm. In all studies, baseline pupil diameter measurements were taken prior to drug administration and then at 0.5, 1, 2, 3 and 4 hours post dose. All studies were done under low-light conditions in which a red photography light is used providing 2-10 Lux of light. The results are shown in FIG. 1 to FIG. 4.

As mentioned in Example 1, it would have been expected that alpha-2-adrenergic receptor pan-agonists such as compounds 2 and 3 and the compound of Formula I (compound 1) would have similar miotic efficacy (peak and duration) in rabbit to that of brimonidine (compound 4). However, both the compounds of entries 2 and 3 have miotic efficacy that is much less than brimonidine, as can be seen from FIG. 1 to FIG. 4. In spite of having similar potency to brimonidine at the alpha-2A-adrenergic receptor, the compound of Formula I unexpectedly is about 30 to about 100 times more potent than brimonidine in the rabbit model (for example, the 0.001% solution of the compound in Formula I in FIG. 3 has a similar dose miotic response curve as seen with the 0.1% solution of brimonidine in FIG. 2 in terms of peak pupil decrease and duration of decrease, with the 0.001% composition of the compound of Formula I therefore having more miotic efficacy than the 0.1% dose tested for brimonidine). The compound of Formula I had the best miotic effect when compared with other alpha adrenergic receptor agonists including brimonidine. For example, as shown in FIG. 3, the compound of Formula I (compound 1) showed a very potent dose miotic response in DB rabbits-Scotopic condition (<10 lux). Furthermore, as shown in FIG. 4, responder analysis of the subjects (rabbits) with >2.5 mm pupil change showed that the compound of Formula I is more efficacious than brimonidine (compound 4) in Dutch Belted rabbits (n=6) under scotopic condition (<10 lux). In particular, FIG. 4 also shows that a greater amount of pupil size reduction can be achieved for a longer amount of time for the Compound of Formula I as compared to brimonidine since virtually all animals dosed with the compound of Formula I had a greater than 2.5 mm reduction in pupil size from baseline at two hours after dosing, and more than half had the same pupil size reduction after 6 hours, whereas much less than half of the animals dosed with brimonidine exhibited the same pupil size reduction even at a half hour after dosing, and virtually none of the animals exhibited the same pupil size reduction after 6 hours.

Figure 2:
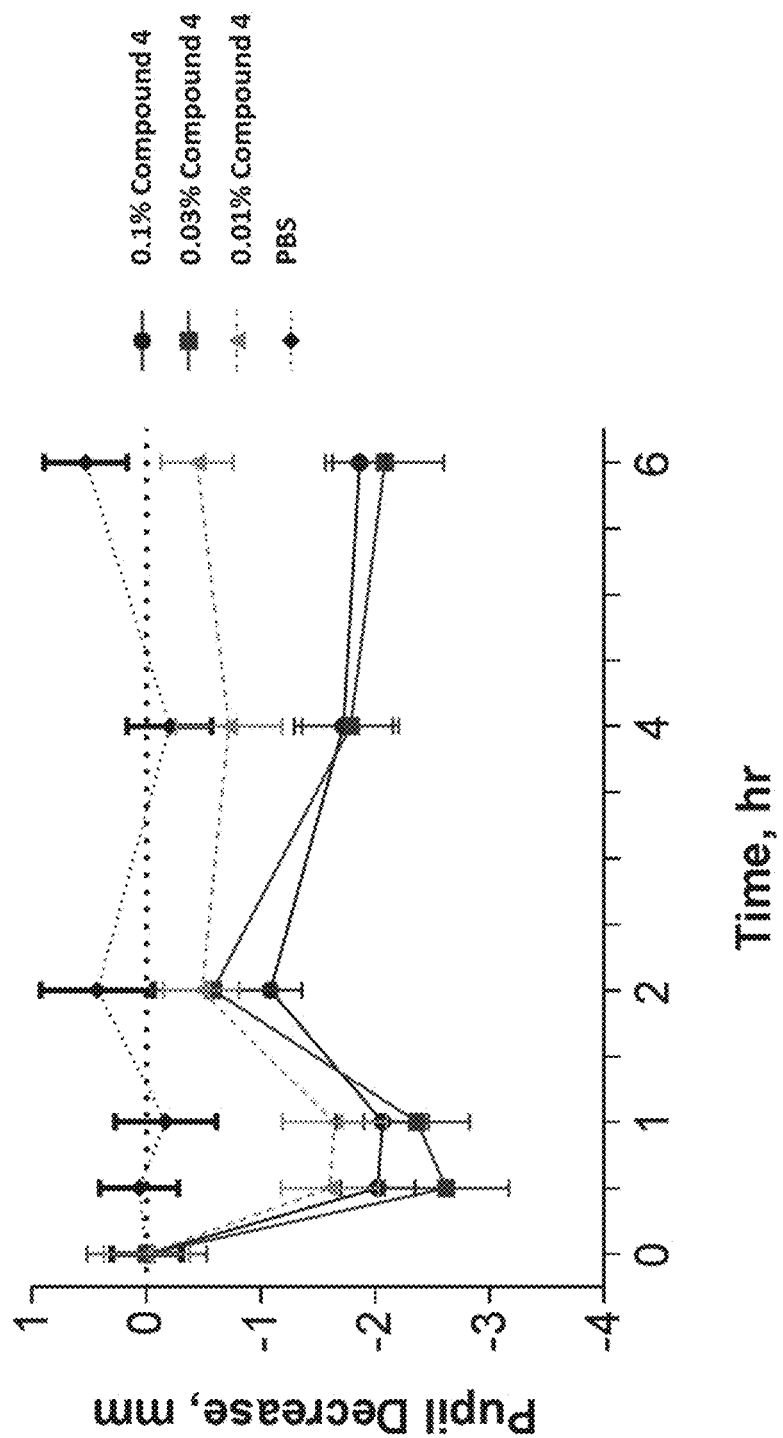
FIG. 2 shows a plot of the dose miotic response curve in Dutch Belted rabbits when topically dosed with brimonidine (compound 4; see Example 1). Percentage amounts are % w:v.
Figure 3:
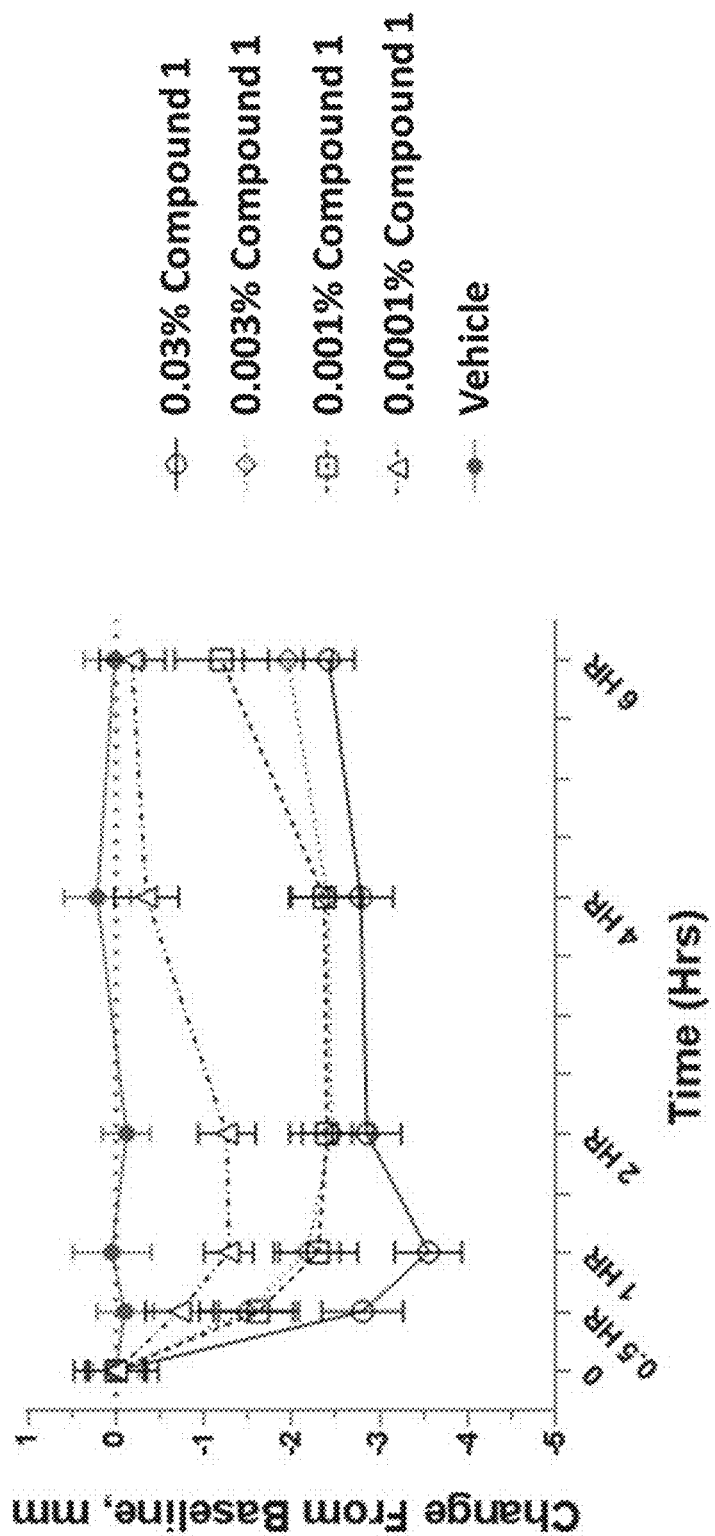
FIG. 3 shows a plot of the dose miotic response curve in Dutch Belted rabbits when topically dosed with the compound of Formula I (compound 1; see Example 1). Percentage amounts are % w:v.
Figure 4:
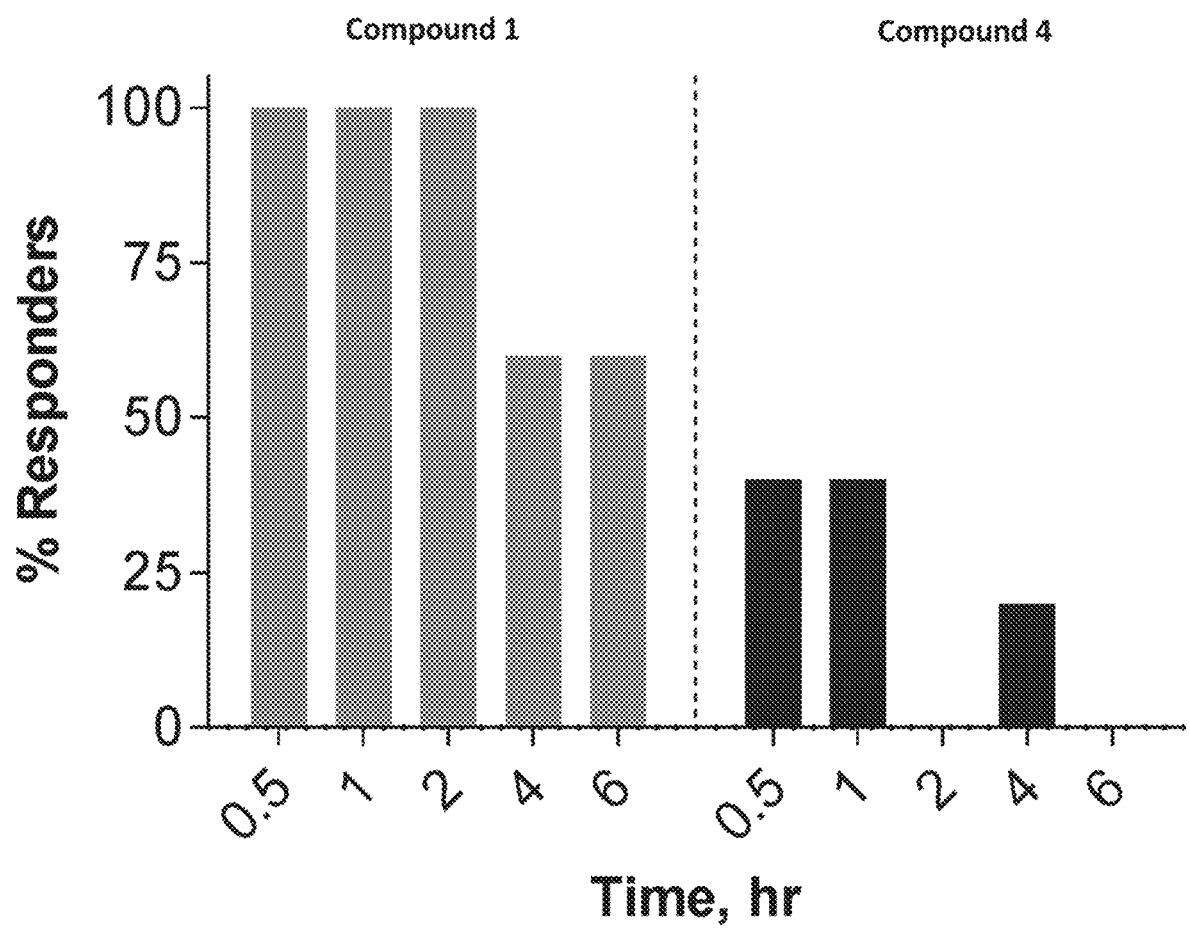
FIG. 4 shows a responder analysis of subjects (rabbits) with >2.5 mm pupil change when dosed with the compound of Formula I (compound 1) or brimonidine (compound 4), both at 0.1% w:v.

Additionally, as can be seen in FIG. 4 and in the comparison of FIGS. 2 and 3, the compound of Formula I shows a greater magnitude of pupil size reduction and therapeutic activity when compared to brimonidine.

Figure 5:
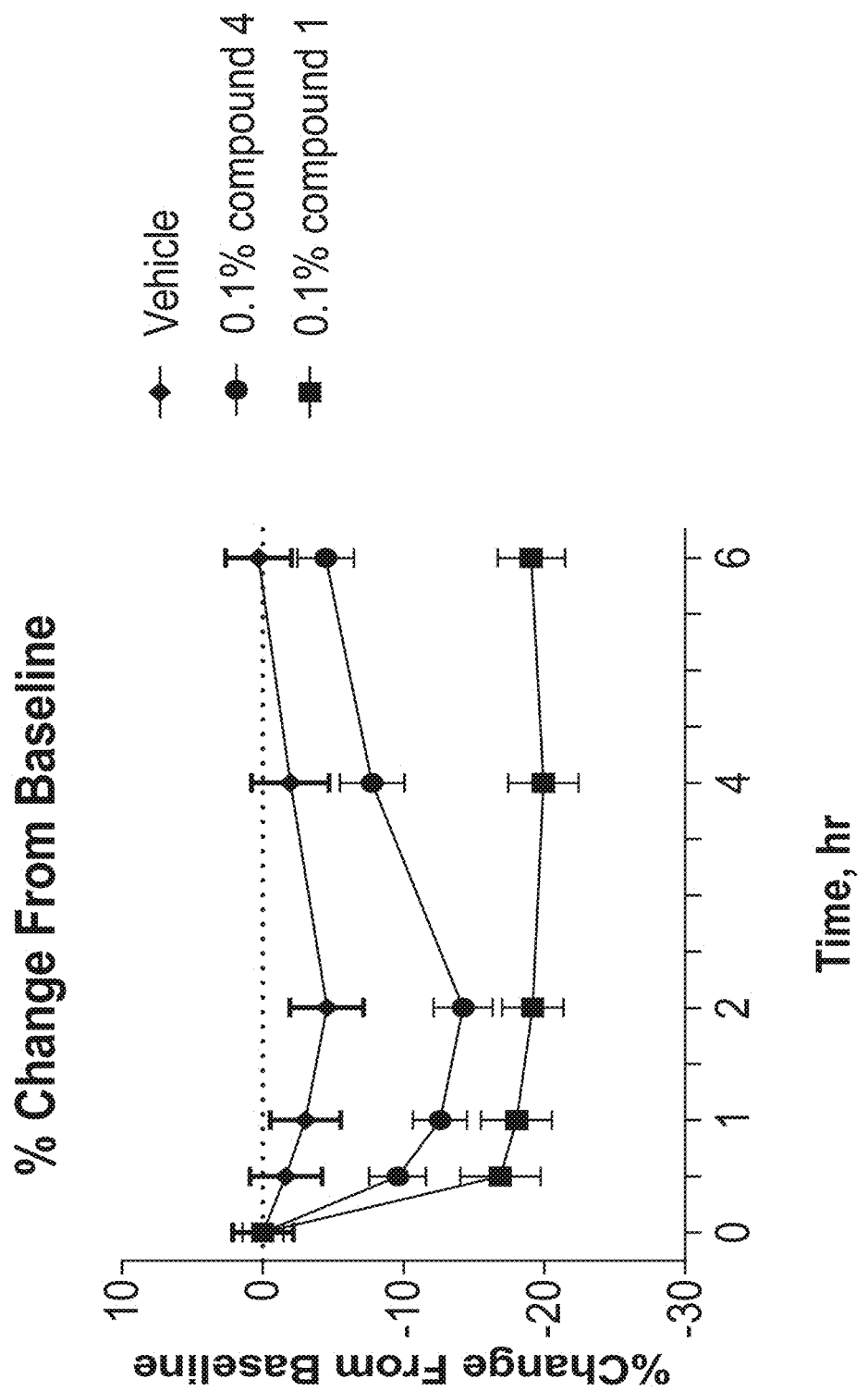
FIG. 5 shows a comparison of brimonidine (compound 4) and the compound of Formula I (compound 1; see Example 1) duration of miotic action after topical dosing in DB rabbits under room light condition. Percentage amounts are % w:v.

In addition, in a similar experiment performed under room lighting conditions, rabbits dosed with the compound of Formula I (Compound 1) still had greater miotic action than brimonidine (Compound 4) both in terms of peak pupil constriction and in terms of duration of action, as can be seen from FIG. 5.

Figure 6:
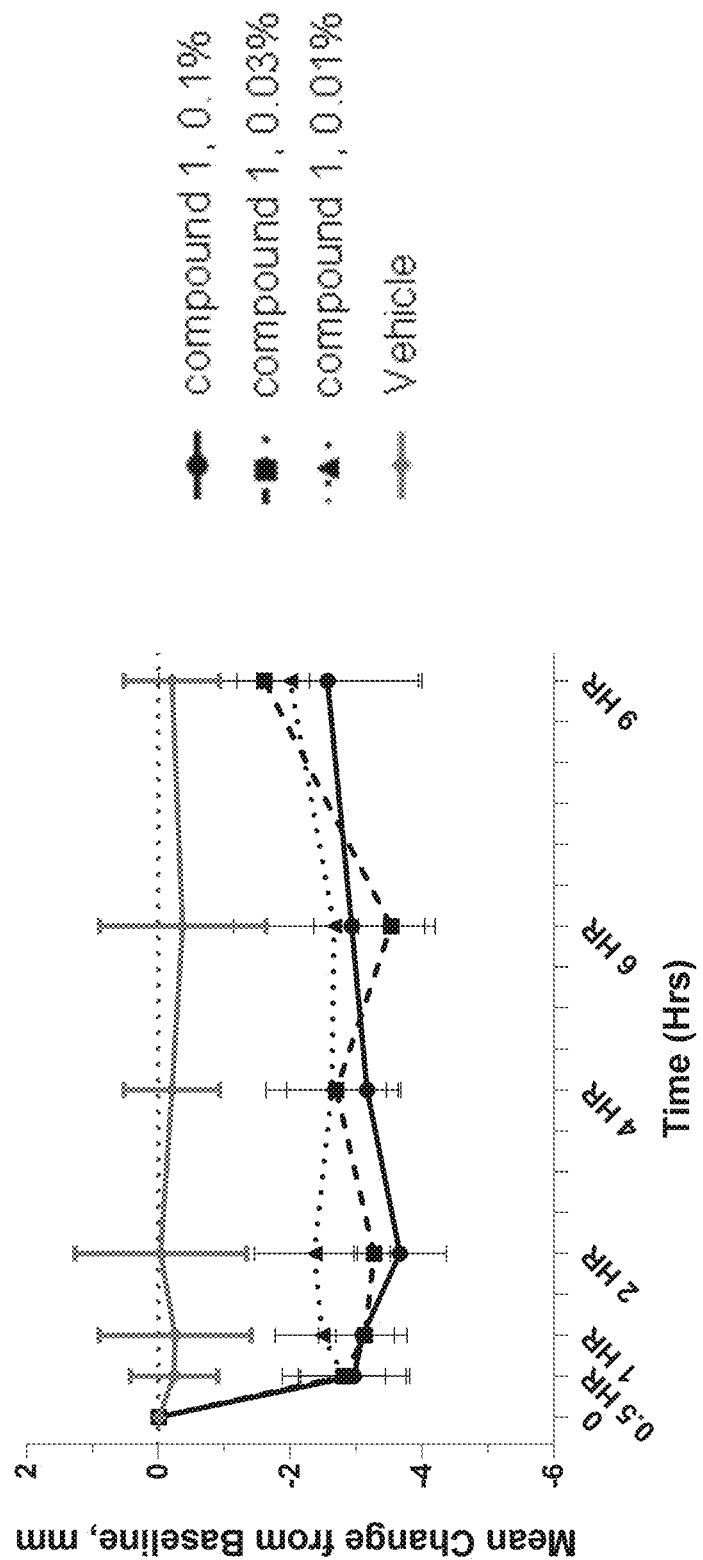
FIG. 6 shows a plot of the dose miotic response curve (over 9 hours) in Dutch Belted rabbits when topically dosed with the compound of Formula I (compound 1; see Example 1). Percentage amounts are % w:v.
Figure 7:
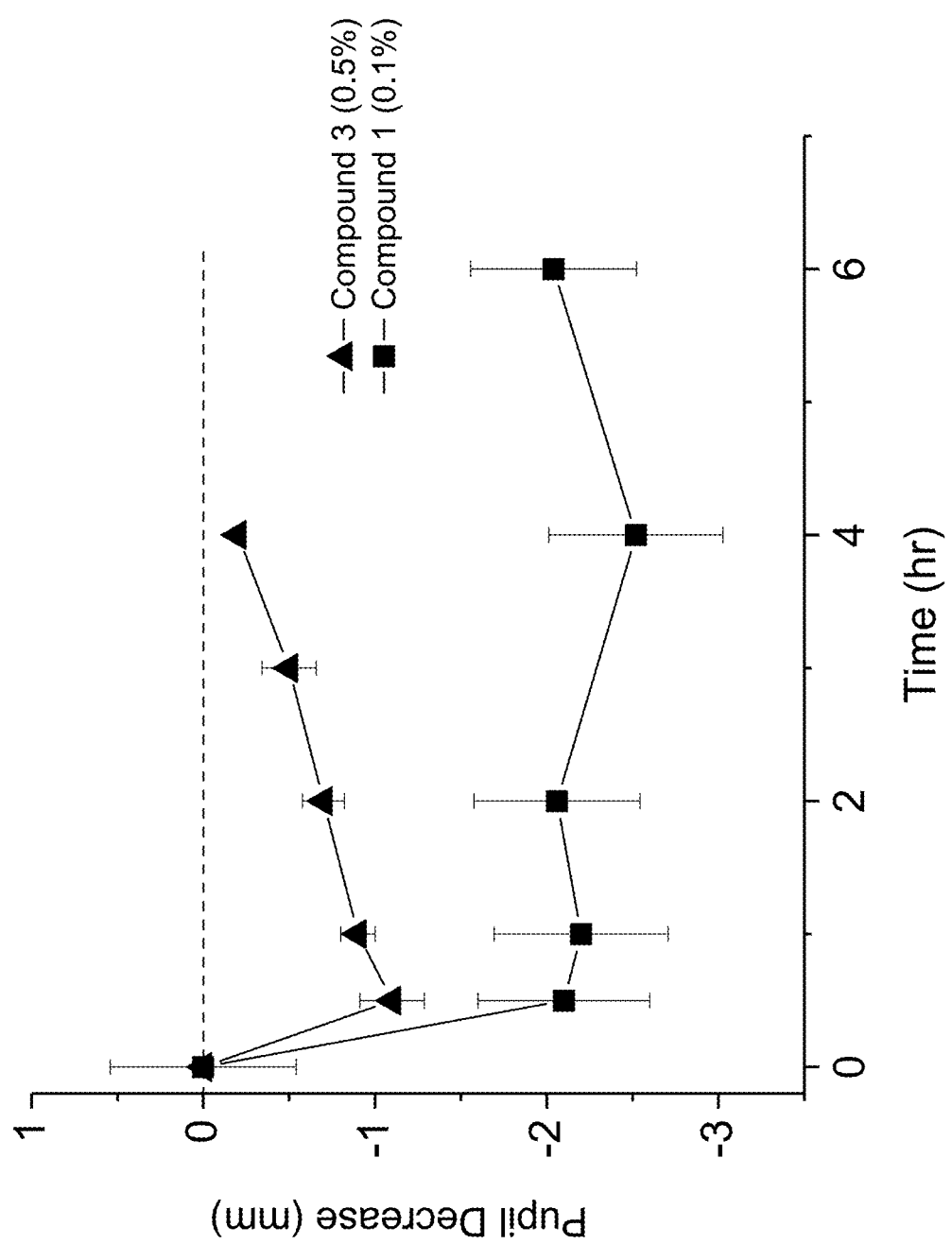
FIG. 7 shows a plot of the comparison of dose miotic response curves in Dutch Belted rabbits when topically dosed with the compound of Formula I (compound 1; see Example 1) or with compound 3 (see Example 1). Percentage amounts are % w:v.

Additionally, as can be seen from FIG. 6, the compound of Formula I (Compound 1) continues to show significant pupil constriction even at 9 hours after dosing. In addition, as shown in FIG. 7, the compound of Formula I also showed a greater effect on pupil constriction when compared to Compound 3.

Such results would not have been expected since based on the in vitro data from Example 1, all the compounds would have been expected to have very similar miotic activity.

Example 3

Melanin Binding

An assay was performed in which the melanin binding of the compound of Formula I was measured and compared to the melanin binding of additional compounds including brimonidine (the binding of which was previously determined by the inventors).

In particular, the compound of Formula I (Compound 1), Compound 2, and a positive control (chloroquine; Compound 5) were tested for binding to synthetic melanin. The testing concentrations ranged from 1.29 ng/mL to 12,500 ng/mL for the compound of Formula I (Compound 1) and Compound 2, and from 19.8 to 8000 ng/mL for chloroquine. Compound stock solutions were prepared in dimethyl sulfoxide with 0.5% or 0.6% (v/v) formic acid (Compound 1 and Compound 2, respectively) or in water (chloroquine) and then further diluted in PBS to the specified curve range and incubated at 37° C. for 1 hour with and without melanin. Aliquots of the PBS only curve were quenched at time zero to be used as stability controls and calibration standards. Following centrifugation, samples were analyzed by LC-MS/MS bioanalysis. Back-calculated concentrations using the assay PBS curve were used for binding and stability calculations. The results of the melanin binding assay and the comparison to previously determined melanin binding of brimonidine can be seen in Table 2.

TABLE 2

| Compound | Structure | Mean % bound across all concentrations |
|---|---|---|
| 1 | 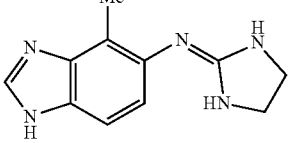 (Formula I) | 8.6 |
| 2 | 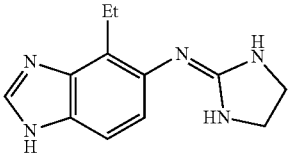 | 9.1 |
| 4 | 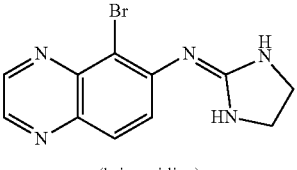 (brimonidine) | 80 |
| 5 | Chloroquine (positive control) | 94.9 |

As can be seen from table 2, the compound of Formula I exhibits significantly and unexpectedly lower binding that other alpha-2-adrenergic receptor agonists including brimonidine. In particular, with mean binding percentages of around 10% or less, the compound of Formula I could be considered to have no significant melanin binding, in contrast to the much more significant binding seen with brimonidine.

Example 4

Treatments of Presbyopia

A 56-year-old woman complains of an inability to focus on text when reading up close, which is interfering with her ability of read documents at work, as well as reading books and news articles. The problem seems worse under lower lighting conditions, such as the dim lighting in a restaurant. The visual degradation had been occurring over time, but in recent months, the woman's inability to focus on text when read close up had been more pronounced such as to interfere with her quality of life. The woman is seen by an ophthalmologist who performs a visual acuity test in which she is asked to read lines of letters on an eye chart without the assistance of glasses or contacts (neither of which she wears anyway). She finds that she is only able to read the first four lines on the chart, when a person with normal vision should be able to read six. Based on the woman's age and results of the test, she is diagnosed with presbyopia. The woman is reluctant to have to obtain reading glasses or wear contact lenses and asks if there are any other medical treatments. She is instructed to administer to her eyes a composition comprising a compound of Formula I one or two times a day. Starting with the first couple of doses, the patient reports improved vision when reading text up close. On a follow-up visit to the ophthalmologist, she is again asked to read lines of letters on an eye chart (she is still administering the composition with the compound of Formula I to her eyes), and this time she is able to read the first six lines, a two line improvement over her previous results prior to administering the compound of Formula I to her eyes.

A 48-year old man has noticed that his near vision has been deteriorating over the last few years such that he often has to hold reading material almost out to arm's length in order to be able to read the print, especially when the ambient light is dim. The man visits his ophthalmologist who performs a basic eye exam and refraction assessment. Based on the examination, the ophthalmologist prescribes a composition comprising brimonidine to constrict the man's pupil to treat the presbyopia, and the man is instructed to administer the composition to his eyes daily as needed. After a week the man returns to his ophthalmologist and indicates that while the brimonidine composition is working effectively to treat the presbyopia (he no longer has to hold reading documents out at almost arm's length), he finds that he must administer the composition three or more times a day. The ophthalmologist switches the man to a composition comprising the compound of Formula I and instructs him to administer the new composition to his eyes as needed as he had done with the brimonidine composition. The ophthalmologist follows up with the man about a week later and the man reports that the composition comprising the compound of Formula I works as well as the brimonidine composition, but unlike the brimonidine composition, the man only need to administer the composition to his eyes once (or sometimes twice) a day as opposed to three or more times a day.

A 66-year-old man reports dissatisfaction with his bifocal glasses, which, due to the two different refractive indices in the component parts of the lenses, have caused him to nearly fall several times when descending stairs. His ophthalmologist, having previously diagnosed him with presbyopia, instructs him to administer once daily to his eyes a composition comprising a compound of Formula I. After administration, the patient finds that his near and distance vision are improved, and that he no longer requires near and distance visual correction with glasses.

A 59-year-old woman who was previously diagnosed with presbyopia wishes to look into alternatives to the glasses and contact lenses that she has been wearing since her diagnosis. Her ophthalmologist prescribes as composition comprising brimonidine to her and instructs her to administer the composition to her eyes as needed. After a few days of administering the composition to her eyes, she calls the ophthalmologist and tells her that although the brimonidine composition is working to improve her vision such that she doesn't need her glasses or contacts to read text when it is up close, she finds that she generally needs to use greater amounts of the composition to achieve satisfactory results than the prescribing information indicates is usually needed and that she is experiencing some of the side effects associated with brimonidine such as sedation. The ophthalmologist notes that the woman has very dark irises and suspects that some amount of the brimonidine (which has fairly high melanin binding) is likely binding to the melanin in the woman's irises thus requiring her to administer more of the brimonidine composition to provide enough free (not bound to melanin) brimonidine to achieve satisfactory effects. The ophthalmologist changes the woman's prescription to be for a composition comprising a compound of Formula I and instructs her to administer the composition to her eyes as she did with the brimonidine composition. About a week later the ophthalmologist follows up with the woman who indicates that she can now obtain a satisfactory improvement in her near-reading vision with less drops of the composition comprising a compound of Formula I than she did with the brimonidine composition and is not experiencing the side effects associated with alpha-2-adrenergic receptor agonists such as sedation.

Example 5

Treatments of Visual Glare, Starbursts, and Halos

A 45-year-old man decides to undergo LASIK surgery. The surgeon who will perform the surgery evaluates the patient and determines that he is a suitable candidate for the surgery, but is told that side effects of the surgery include visual glare, visual starbursts, and visual halos, especially at night. The surgeon performs the surgery without any noticeable issues and the patient is discharged. A day later the patient drives home during the evening for the first time since the surgery and notices what appear to be starbursts of light emanating from the headlights and rear lights of other cars, as well as from street lights, and also glare coming from those light sources that interfere with is vision. The patient also observes diffuse rings around some of the street lights and illuminated street signs. Upon consultation, the surgeon confirms that such visual disturbances are indeed the visual glare, visual starburst, and visual halo side effects often seen after LASIK surgery, and the patient is prescribed a composition comprising the compound of Formula I, which the patient administers to his eyes in accordance with the package instructions. The next time the patient drives home during the evening, the glare, starbursts, and halos are significantly reduced such that he is no longer bothered by them.

A 61-year-old woman decides that she wishes to undergo LASIK surgery so as to no longer need to wear glasses. After being evaluated by a surgeon she is found to be a viable candidate for the procedure. The woman undergoes the procedure and is prescribed a composition comprising brimonidine and instructed to administer the composition to her eyes as needed should she develop any visual glare, visual starbursts, and visual halos, which are common side effects of LASIK. The first time she drives at night after the procedure she indeed notices visual glare, as well as starbursts and halos around light sources and some illuminated signs. As advised by her surgeon, she begins administering the brimonidine composition before here early morning and nighttime commutes. However, she finds that she generally needs to administer more than the standard dosing in order to have a satisfactory effect in reducing the visual disturbances, and the increased amount of brimonidine is having some side effects such as sedation. The woman visits her surgeon and tells her of the situation. The surgeon indicates that alpha-2-adrenergic receptor agonists such as brimonidine can sometimes be associated with side effects such as sedation. The surgeon believes that the problem may be that the woman's dark irises might be binding the brimonidine, since brimonidine is known to bind to melanin, and that the woman might be requiring the increased doses of the brimonidine due to this binding effect. The surgeon then prescribes a composition comprising a compound of Formula I to the woman and instructs her to administer the new composition to her eyes as needed as she had done with the brimonidine composition. The woman is then instructed to follow up with the surgeon after her next night drive. The woman does as instructed and reports back to the surgeon indicating that she needed much less drops of the composition with Formula I than she did with the brimonidine composition in order to makes the visual glare, visual starbursts, and visual halos subside.

A 59-year-old man has been found as a viable candidate for LASIK surgery and chooses to undergo the procedure rather than have to continuing wearing glasses or contacts. The man is a long-distance truck driver and he works a long schedule in which he drives for 9 to 13 hours (sometimes more) at night and early morning and sleeps during the day. Because the man's driving route is located in a norther region of the United States, almost all of the man's 9 to 13 (or more) hours of night driving are in darkness, especially in the winter. The man undergoes the surgery, but is told that some LASIK patients can have visual disturbances such as visual glare, visual starbursts, and visual halos, especially at night. Given that the man's work schedule, he is given a prescription for a composition comprising brimonidine and told to administer the composition to his eyes as needed should he experience the nighttime visual disturbances. Shortly after the surgery, when the man returns to his night driving duties, he notices visual glare, visual starbursts, and visual halos coming from light sources such as headlights and taillights and illuminated highway signs. The man does as his surgeon ordered and begins administering the brimonidine composition to his eyes. He finds that even though the brimonidine composition reduces the visual glare, visual starbursts, and visual halos, he has to administer the composition 3 or 4 times during his long drive. He contacts his ophthalmologist and asks if there are any other medicines he can use to deal with the visual disturbances which might be longer acting. The ophthalmologist prescribes a composition comprising the compound of Formula I and is told to use that composition instead. The man happily finds out that he only needs to administer the composition comprising the compound of Formula I only once (or sometimes twice) during his long drive.

Example 6

Night Vision Improvements

A 62-year-old woman has noticed that she is having issues seeing the street names on street signs with good contrast when she is driving at night. The woman consults with her ophthalmologist who, upon hearing the patient's description and performing a visual acuity test under low light conditions, prescribes a composition comprising the compound of Formula I, which the patient administers to her eyes in accordance with the package instructions. The next time the patient is driving at night, the patient finds that she can see with much better contrast and is thus better able to read street signs.

A 45-year-old man works as a nighttime security guard and complains that he is having issues seeing objects with good contrast at night. Because this interferes with his job, he meets with an ophthalmologist who prescribes a composition comprising brimonidine and instructs the man to administer the composition to his eyes. However, he finds that he often needs to administer fairly large amounts of the composition to his eyes in order to obtain a satisfactory effect, and these larger amounts are beginning to cause side effects that are sometimes seem with brimonidine (in particular sedation). He consults with his ophthalmologist who believes that the problem may be that the brimonidine is being bound by the melanin in the man's irises, which are quite dark. The ophthalmologist switches the man to a composition comprising the compound of Formula I and instructs him to administer that composition instead of the brimonidine composition and report the results back to the ophthalmologist. The man does so, and when he reports back to the ophthalmologist a few days later, he indicates that he can obtain satisfactory night vision improvement with much less of the composition comprising the compound of Formula I and consequently does not suffer from the side effects that he was previously experiencing.

Example 7

Treatments of Night Myopia

A 56-year-old woman notices that, although she has no significant problems with distance vision during the day, during the night she seems to have a difficult time focusing of distant objects (e.g. street signs). She goes to see an ophthalmologist who performs some visual acuity testes under both normal lighting conditions and under low light conditions. The ophthalmologist confirms that the woman does not have any significant issues with distance vision under the normal lighting conditions, but that she does suffer from myopia under the low light conditions. She is prescribed a composition with the compound of Formula I, which she administers to her eyes in accordance with the package instructions. The patient the finds that her ability to focus on distant objects at night is now as good as her ability to do so during the day.

A 61-year-old man who works a full 9 to 10-hour work schedule almost exclusively at night has noticed that he has problems focusing on distant objects at night while his colleagues of similar age do not have that problem. He also notices that he does not, in turn, have the same problem focusing on distant objects during the day. He visits an ophthalmologist who diagnoses the man with night myopia and prescribes a composition comprising brimonidine and instructs him to administer it to his eyes as needed. The man finds that administering the brimonidine composition to his eyes gives him a notable improvement is his ability to focus on distant objects at night, but it has a fairly short duration of action such that he often needs to administer the composition to his eyes three or four times during his waking hours so as to maintain a satisfactory effect. He calls his ophthalmologist who then prescribes a composition comprising the compound of Formula I and instructs him to use that composition instead. The man does so and finds that he now only needs to administer the composition only once or twice during his waking hours.

Throughout this specification reference is made to publications such as US and foreign patent applications, journal articles, book chapters, and others. All such publications are expressly incorporated by reference in their entirety, including supplemental/supporting information sections published with the corresponding references, for all purposes unless otherwise indicated. To the extent that any recitations in the incorporated references conflict with any recitations herein, the recitations herein will control.

The foregoing descriptions details methods that can be employed to treat various ocular conditions, and represents the best mode contemplated. It should not be construed as limiting the overall scope hereof; rather, the ambit of the present disclosure is to be governed only by the lawful construction of the appended claims.

What is claimed is:

1. A method of treating an ocular condition in an individual in need of such treatment, the method comprising administering to the individual a therapeutically effective amount of a compound of Formula I:

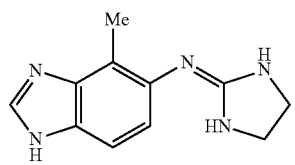

Formula I or a pharmaceutically acceptable salt thereof; wherein the ocular condition is selected from the group consisting of presbyopia, visual glare, visual starbursts, visual halos, and night myopia; wherein the therapeutically effective amount of the compound of Formula I or pharmaceutically acceptable salt thereof is administered topically to one or both eyes of the individual as a pharmaceutically acceptable composition comprising the therapeutically effective amount of the compound of Formula I or a pharmaceutically acceptable salt thereof and a pharmaceutically acceptable excipient; and wherein the pharmaceutically acceptable composition comprises the compound of Formula I in an amount of from 0.01% (w/v) to 0.3% (w/v).

2. The method of claim 1, wherein the ocular condition is presbyopia.

3. The method of claim 1, wherein the ocular condition is visual glare.

4. The method of claim 1, wherein the ocular condition is visual starbursts.

5. The method of claim 1, wherein the ocular condition is visual halos.

6. The method of claim 1, wherein the ocular condition is night myopia.

7. The method of claim 1, wherein the pharmaceutically acceptable composition comprises the compound of Formula I in an amount of 0.01% (w/v).

8. The method of claim 1, wherein the pharmaceutically acceptable composition comprises the compound of Formula I in an amount of 0.03% (w/v).

9. The method of claim 1, wherein the pharmaceutically acceptable composition comprises the compound of Formula I in an amount of 0.1% (w/v).

10. The method of claim 1, wherein the pharmaceutically acceptable composition comprises the compound of Formula I in an amount of 0.3% (w/v).

11. The method of claim 1, wherein the method comprises administering a pharmaceutically acceptable salt of compound 1 and wherein the pharmaceutically acceptable salt is a hydrochloride salt.

* * * * *